United States Patent
Wang et al.

(10) Patent No.: US 11,261,479 B2
(45) Date of Patent: Mar. 1, 2022

(54) METHODS AND COMPOSITIONS FOR ENRICHMENT OF TARGET NUCLEIC ACIDS

(71) Applicant: Chapter Diagnostics, Inc., Menlo Park, CA (US)

(72) Inventors: Chunlin Wang, Menlo Park, CA (US); Zhihai Ma, Mountain View, CA (US); Baback Gharizadeh, Menlo Park, CA (US)

(73) Assignee: Chapter Diagnostics, Inc., Menlo Park, CA (US)

( * ) Notice: Subject to any disclaimer, the term of this patent is extended or adjusted under 35 U.S.C. 154(b) by 187 days.

(21) Appl. No.: 16/392,114

(22) Filed: Apr. 23, 2019

(65) Prior Publication Data

US 2020/0340035 A1    Oct. 29, 2020

(51) Int. Cl.
    *C12Q 1/6806* (2018.01)
    *C12Q 1/6886* (2018.01)

(52) U.S. Cl.
    CPC ......... *C12Q 1/6806* (2013.01); *C12Q 1/6886* (2013.01); *C12Q 2600/156* (2013.01); *C12Q 2600/16* (2013.01)

(58) Field of Classification Search
    CPC .............. C12Q 2525/191; C12Q 2600/16
    See application file for complete search history.

(56) References Cited

U.S. PATENT DOCUMENTS

| 9,487,828 | B2 | 11/2016 | Iafrate et al. |
| 2007/0128624 | A1 | 6/2007 | Gormley et al. |
| 2012/0270739 | A1 | 10/2012 | Rava et al. |
| 2018/0251848 | A1 | 9/2018 | Diehn et al. |

FOREIGN PATENT DOCUMENTS

| WO | 2002034939 A3 | 1/2003 |
| WO | 2017142989 A1 | 8/2017 |

OTHER PUBLICATIONS

Angers M, et al. Optimal conditions to use Pfu exo(-) DNA polymerase for highly efficient ligation-mediated polymerase chain reaction protocols. Nucleic Acids Res. Aug. 15, 2001;29(16):E83.
Chenchik A, et al. Full-Length cDNA Cloning and Determination of mRNA 5' and 3' Ends by Amplification of Adaptor-Ligated cDNA. Biotechniques. Sep. 1996;21(3):526-34.
Dai SM, et al. Ligation-mediated PCR for quantitative in vivo footprinting. Nat Biotechnol. Oct. 2000;18(10):1108-11.

(Continued)

*Primary Examiner* — Teresa E Strzelecka
(74) *Attorney, Agent, or Firm* — Maynard Cooper & Gale, P. C.; Matthew J. Parker

(57) ABSTRACT

The present disclosure relates to a method of target enrichment and amplification of selective target regions of genomes or nucleic acid samples and further analysis by systems such as NGS. The disclosure provides methods and kits that can be used in numerous downstream procedures including DNA sequencing. The disclosed methods can be utilized to sequence the target nucleic acid sequences such as to detect the presence of genetic variations for biological assays, assessment of disease, to count copies of target regions, and to allow such target enrichment prior to sequencing.

15 Claims, 9 Drawing Sheets

(56) References Cited

OTHER PUBLICATIONS

Espinoza CR, Feeney AJ. Quantifying chromatin accessibility of individual gene family members by combining ligation-mediated PCR with real-time PCR. Biotechniques. Oct. 2006;41(4):404, 406, 408.

Garrity PA, Wold BJ. Effects of different DNA polymerases in ligation-mediated PCR: enhanced genomic sequencing and in vivo footprinting. Proc Natl Acad Sci U S A. Feb. 1, 1992;89(3):1021-5.

Hermann SR, et al. Single-primer amplification of flanking sequences. Biotechniques. Dec. 2000;29(6):1176-8, 1180.

Iwahana H, et al. PCR with End Trimming and Cassette Ligation: A Rapid Method to Clone Exon—Intron Boundaries and a 5'-Upstream Sequence of Genomic DNA Based on a cDNA Sequence. Genome Res. 1994. 4:19-25.

Ji J, Braam J. Restriction site extension PCR: a novel method for high-throughput characterization of tagged DNA fragments and genome walking. PLoS One. May 11, 2010 ;5(5):e10577.

Kilstrup M, Kristiansen KN. Rapid genome walking: a simplified oligo-cassette mediated polymerase chain reaction using a single genome-specific primer. Nucleic Acids Res. Jun. 1, 2000;28(11):E55.

Mueller PR, et al. Ligation-mediated PCR for genomic sequencing and footprinting. Curr Protoc Mol Biol. Nov. 2001;Chapter 15:Unit 15.3.

Mueller PR, Wold B. In vivo footprinting of a muscle specific enhancer by ligation mediated PCR. Science. Nov. 10, 1989;246(4931):780-6.

O'Malley RC, et al. An adapter ligation-mediated PCR method for high-throughput mapping of T-DNA inserts in the Arabidopsis genome. Nat Protoc. 2007;2(11):2910-7.

Pfeifer GP, Riggs AD. Genomic sequencing by ligation-mediated PCR. Mol Biotechnol. Jun. 1996;5(3):281-8.

Pfeifer GP, Tommasi S. In vivo footprinting using UV light and ligation-mediated PCR. Methods Mol Biol. 2000;130:13-27.

Quivy JP, Becker PB. An improved protocol for genomic sequencing and footprinting by ligation-mediated PCR. Nucleic Acids Res. Jun. 1, 19931 ;21 (11 ):2779-81.

Quivy JP, Becker PB. Direct Dideoxy Sequencing of Genomic DNA by Ligation-Mediated PCR. Biotechniques. Feb. 1994;16(2):238-41.

Rosenthal A, Jones DS. Genomic walking and sequencing by oligo-cassette mediated polymerase chain reaction. Nucleic Acids Res. May 2, 19905;18(10):3095-6.

SantaLucia J Jr. A unified view of polymer, dumbbell, and oligonucleotide DNA nearest-neighbor thermodynamics, Proc. Natl. Acad. Sci. USA. 1998; 95:1460-65.

Shyamala V, Ames GF. Genome walking by single-specific-primer polymerase chain reaction: SSP-PCR. Gene. Dec. 7, 1989;84(1):1-8.

Shyamala V, Ferro-Luzzi Ames G. Single Specific Primer-Polymerase Chain Reaction (SSP-PCR) and Genome Walking. Methods Mol Biol. 1993;15:339-48.

Steigerwald SD, et al. Ligation-mediated PCR improves the sensitivity of methylation analysis by restriction enzymes and detection of specific DNA strand breaks. Nucleic Acids Res. Mar. 2, 19905; 18(6): 1435-9.

Tonooka Y, Fujishima M. Comparison and critical evaluation of PCR-mediated methods to walk along the sequence of genomic DNA. Appl Microbiol Biotechnol. Nov. 2009;85(1):37-43.

Zhang ZW, Heng ZC. Randomized terminal linker-dependent PCR: a versatile and sensitive method for detection of DNA damage. Biomed Environ Sci. Sep. 2002;15(3):203-8.

Zheng Z, et al. Anchored multiplex PCR for targeted next-generation sequencing. Nat Med. Dec. 2014;20(12):1479-84.

Figure 6
Target strand-Specific Amplification of Exemplary EGFR Exons 18-21 in Two Separate Test Reactions
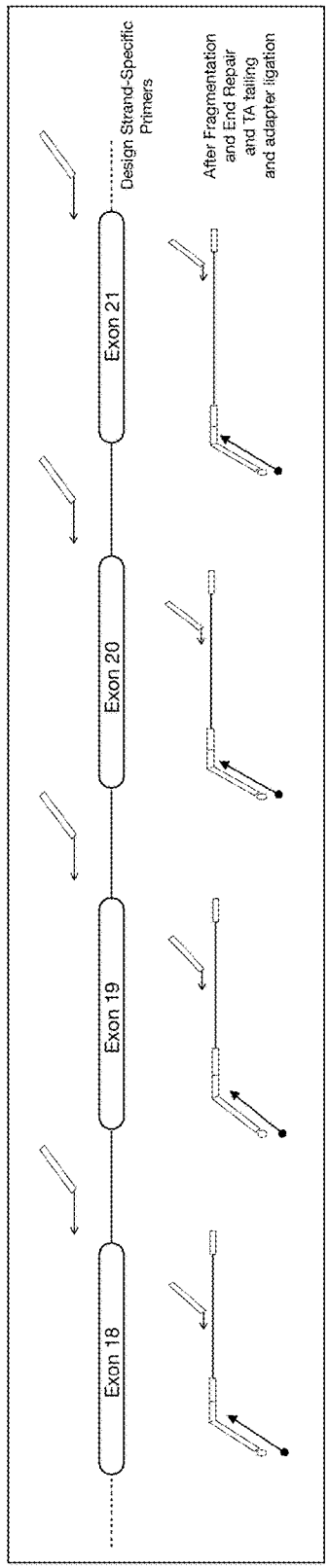
First Test Reaction with Forward Strand-Specific primers for positive strand
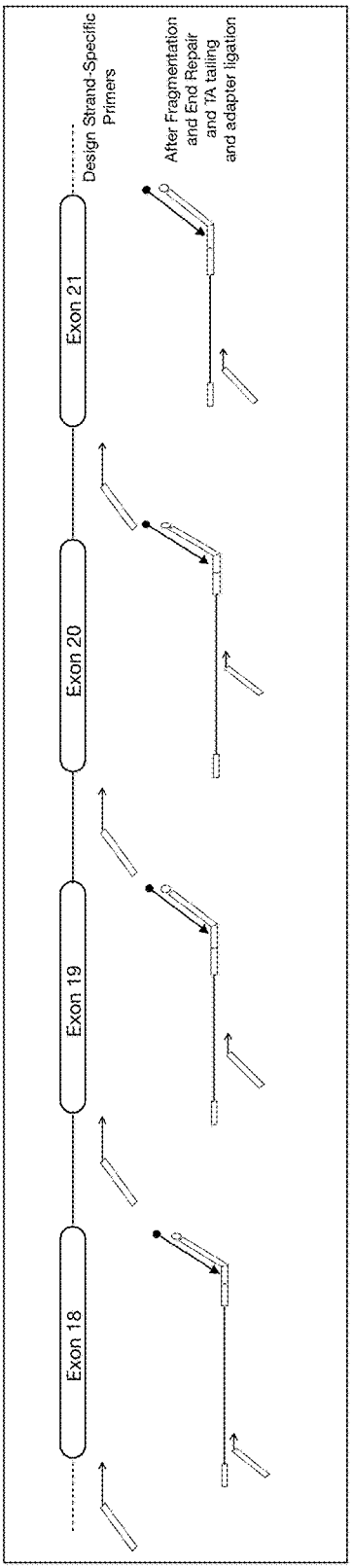
Second Test Reaction with Reverse Strand-Specific Primers for negative strand Figure 9
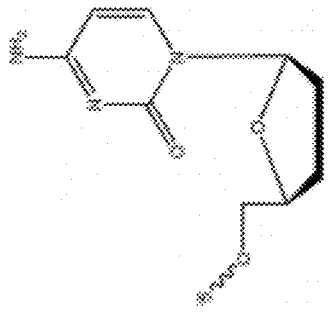
B) Dideoxycytidine (ddC)
D) 3' Hexanediol
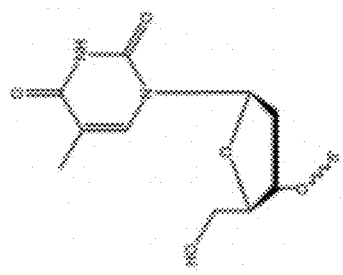
A) Inverted dT
C) 3' C3 spacer

METHODS AND COMPOSITIONS FOR ENRICHMENT OF TARGET NUCLEIC ACIDS

BACKGROUND OF THE INVENTION

Multiplex amplification of target nucleic acid sequences has allowed a great number of applications in a single polymerase chain reaction (PCR). Many cancers and inherited diseases are complex diseases and may be linked to multiple genes, and the mutations involved may be heterozygous. Moreover, these mutations may exist in a small quantity in an isolated sample. By combining multiplex amplification-based target enrichment of genes and massive parallel sequencing, it is possible to differentiate homozygous and heterozygous mutations and a small quantity of mutations in a sample with limited input DNA.

Multiplex amplification can amplify multiple targets of interest and advantageously increase the number of target regions that can be amplified in a single reaction, starting from limited amounts of DNA, such that hundreds to thousands of target regions can be amplified simultaneously for sequencing. The selective multiplex amplification has a wide range of applications in clinical and research settings and can be used for mutation detection and analysis, single nucleotide polymorphisms (SNPs), microbial and viral detection, deletions and insertions, genotyping, copy number variations (CNVs), epigenetic and methylation analysis, gene expression, and transcriptome analysis. These applications can be used for the diagnosis, prognosis and treatment of disease.

Using multiple target-specific primers in a single PCR reaction allows multiplex amplification of selective targets in an efficient manner, saving cost and labor, and increasing throughput. Increasing the number of oligonucleotide primers in a reaction, however, may introduce primer cross-reactivity and produce amplification artifacts such as primer-dimers. Furthermore, in highly multiplex amplification reaction, some primers might be suppressed to be working, which causes target dropouts. These amplification artifacts may consume amplification components and reagents such as dNTPs and DNA polymerase, affecting the overall efficiency and quality of the amplification reaction. These artifacts from highly multiplex amplifications may also affect the downstream procedures such as sample preparation for next-generation sequencing (NGS). In such circumstances, the amplification artifacts can consume NGS read results, generating overly dominant, non-informative sequencing reads.

As the number of nucleic acid target regions for selective amplification is increased, proportionally more primers are needed in the same reaction. Higher primer numbers and increasing overall concentrations of primers in a single test reaction may increase the likelihood of generating amplification artifacts such as primer-dimers, off-target amplifications, superamplicons, and target dropout due to interference between primers, affecting the downstream steps. A common approach to avoid or minimize these amplification artifacts is the use of commercial or in-house software packages to design primers for multiplex amplification assays to avoid or lower the chance of primer-dimer formations and off-target priming. This can be done by: 1) using stringent design considerations to design target specific primers with no or minimal primer interactions; and 2) grouping the primers into optimal subsets of non-overlapping pools to avoid artifacts.

Target-enrichment methods selectively capture genomic regions from a DNA sample before sequencing. The current problem with target enrichment is the need to achieve higher specificity and uniformity, which currently requires fewer sequencing reads to generate adequate coverage and sequence data for the downstream analysis. In certain applications such as cancer or genetic diseases, much deeper sequencing is needed to detect, identify or verify somatic mutations with high specificity and uniformity in the panel. As such, there is a need for methods and/or compositions that enable amplification-based target enrichment of a significant number of target-specific sequences with minimal amplification artifacts, such as primer-dimers and off-target amplification products, as well as eliminating or minimizing primer grouping for separate test reactions, which would necessitate additional steps compared to a single multiplex reaction.

SUMMARY OF THE INVENTION

In some embodiments, the present disclosure relates to a method comprising the steps of: 1) directionally ligating partially double-stranded blocking adapters to the ends of one or more nucleic acid samples; 2) combining the resulting fragments with biotin-labeled universal sequence primer A and: (a) one or more forward strand-specific primers in one test reaction; and (b) one or more reverse strand-specific primers in a second test reaction, wherein both forward and reverse strand-specific primers comprise a second universal sequence that is different from the universal primer within the partially double-stranded adapter; 3) subjecting each test reaction to amplification under amplification conditions to generate amplicons; 4) isolating the amplicons by binding streptavidin-coated beads to the amplicons; 5) subjecting a portion of the amplicons from each test reaction to further amplification using universal sequence primers complementary to the universal sequence to generate final amplicons; and 6) preparing and normalizing the final amplicons for NGS. In some embodiments, the method further comprises at least one additional set of forward strand-specific primers in at least one additional test reaction. In some embodiments, the method further comprises at least one additional set of reverse strand-specific primers in at least one additional test reaction.

In some embodiments, prior to ligation of the partially double-stranded blocking adapters, nucleic acids from genomic DNA are fragmented by physical shearing or chemical/enzymatic treatment and the resulting DNA fragments are then subjected to end-repair and dA-tailing. In some embodiments, prior to ligation of the partially double-stranded blocking adapters, RNA is subjected to reverse transcription reaction to generate double-stranded cDNA. In some embodiments, the double-stranded cDNA can be subjected to fragmentation. In some embodiments, the double-stranded cDNA is subjected to end-repair and dA-tailing prior to partially double-stranded blocking adapter ligation. In some embodiments, the method further comprises the step of subjecting the final amplicons to NGS, and analyzing the sequence data by a software algorithm to generate sequencing read results; and measuring allele counts at polymorphic sites.

In some embodiments, strand L of the partially double-stranded blocking adapter further comprises a barcode sequence to label sample source. In some embodiments, strand L of the partially double-stranded blocking adapter further comprises a unique molecular identifier (UMI). In some embodiments, strand L of the partially double-stranded blocking adapter further comprises nucleic acid sequences that are not complementary to nucleic acids targets in the one or more nucleic acid samples. In some embodiments, strand L of the partially double-stranded blocking adapter is configured to block polymerase extension.

In some embodiments, the one or more nucleic acid samples comprise genomic DNA, cDNA or mRNA. In some embodiments, the one or more nucleic acid samples are isolated from a single cell. In some embodiments, the one or more nucleic acid samples comprise circulating cfDNA (see, e.g., FIG. 4). In some embodiments, circulating cfDNA is obtained from a maternal subject. In some embodiments, the nucleic acid sample comprises nucleic acid molecules obtained from blood, serum, plasma, spinal fluid, urine, tissue, saliva, biopsies, sputum, swabs, surgical resections, cervical swabs, tears, tumor tissue, FNA, circulating cfDNA, and ctDNA, scrapings, swabs, mucus, urine, semen, hair, other non-restricting clinical or laboratory obtained samples or a forensic sample. In some embodiments, each of the one or more nucleic acids samples is a mixture of maternal and fetal DNA from a pregnant woman. In some embodiments, the each of the one or more nucleic acid samples is cell-free DNA from blood plasma of a pregnant woman.

In some embodiments of the method, each of the forward strand-specific primers and reverse strand-specific primers are configured to generate no or minimal cross-hybridization or primer-primer interactions with the other forward-strand specific primers and reverse-strand specific primers. In some embodiments of the method, each of the forward strand-specific primers and reverse strand-specific primers are configured to avoid or minimize off-target priming. In some embodiments of the method, each of the forward strand-specific primers and reverse strand-specific primers are configured to have no more than minimal self-complementary structure. In some embodiments of the method, each of the forward strand-specific primers and reverse strand-specific primers are configured not to form a secondary structure, such as hairpins or loops.

In some embodiments of the method, the nucleic acid sequences targeted by the at least one forward strand-specific primer and at least one reverse strand-specific primer comprise one or more mutations that are associated with disease, cancer, disorders, infections, pharmacogenetic drug treatment (companion diagnostic), drug resistance or drug antibiotic resistance or aneuploidy or trisomy in a gestating fetus. In some embodiments, the disease is related to one or more autoimmune, cardiovascular, developmental, metabolic, neurological, or neuromuscular disorders.

In some embodiments, the disclosure relates to a kit comprising at least one forward strand-specific primer, at least one reverse strand-specific primer, and two common primers A and B. In some embodiments, the kit further comprises at least one partially double-stranded blocking adapter. In some embodiments, the at least one forward strand-specific primer and at least one reverse strand-specific primer both comprise a universal sequence B. In some embodiments, the kit comprises at least: 10; 20; 100; 500; 1,000; 2,500; 5,000; 10,000; 25,000; 50,000; 80,000; 100,000; or 150,000 forward strand-specific primers and reverse strand-specific primers. In some embodiments, the sequence complementary to a target nucleic acid sequence of interest in the at least one forward strand-specific primer and the at least one reverse strand-specific primer where gene-specific portion is about 15 to 40 bases in length.

In some embodiments of the kit, the nucleic acid sequences targeted by the at least one forward strand-specific primer and at least one reverse strand-specific primer comprise one or more mutations that are associated with disease, cancer, disorders, infections, pharmacogenetic drug treatment (companion diagnostic), drug resistance or drug antibiotic resistance or aneuploidy or trisomy in a gestating fetus. In some embodiments, the disease is related to one or more autoimmune, cardiovascular, developmental, metabolic, neurological, or neuromuscular disorders.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 6 depicts an illustration of an example of EGFR exon 18-21 using strand-specific approach in two test reactions. In first reaction, a plurality of forward target strand-specific primers and biotin-labeled common primer A are applied for positive strand target specific amplification EGFR exons and in second reaction reverse target strand-specific primers and biotin-labeled common primer A are applied for negative strand target specific amplification EGFR exons.

FIG. 9 shows example blocker for ligation or polymerase extension at 3' end of adapter. A) inverted T, Inverted dT can be incorporated at the 3'-end of an oligo, leading to a 3'-3' linkage which inhibits both degradation by 3' exonucleases and extension by DNA polymerases. B) Dideoxycytidine (ddC) is a 3' chain terminator that prevents 3' extension by DNA polymerases. C) C3 spacer can be incorporated at 3'-end of oligo to block DNA polymerase extension and ligation, D) Hexanediol is a six carbon glycol spacer that is capable of blocking extension by DNA polymerases and ligation

DETAILED DESCRIPTION

Figure 1:
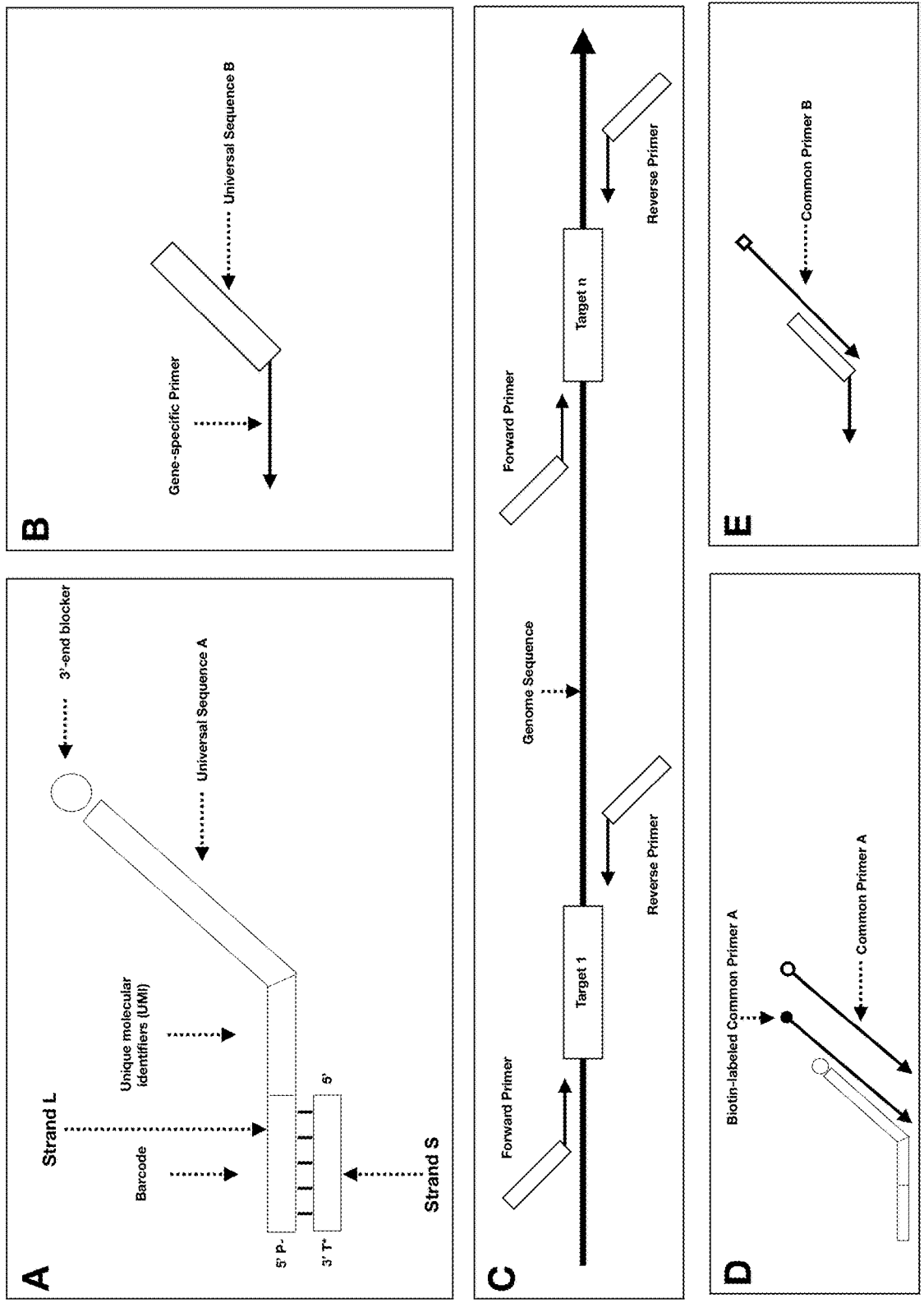
FIG. 1 illustrates adapter and primers used in this disclosure. Panel A depicts a schematic image of partially double-stranded blocking adapter for ligation to double-stranded DNA or cDNA. The partially double-stranded blocking adapter comprises a longer strand (strand L) and a short strand (strand S). Strand L comprises a barcode portion at 5' end, a UMI portion in the middle, and a universal sequence A portion at the 3' end. The 3'-end of strand L is configured with special base or special chemical unit (see FIG. 9) to prevent polymerase extension. Strand S is paired with the 5' end of strand L. In addition, strand S has a terminal T at the 3' end, which is not paired with strand L. The T overhang will pair with the A-tail added to library fragments in the ligation reaction. Although a terminal T is shown at the 3' end of strand S, other bases such as A, C or G could also be used with corresponding adjustment for T-tailing, G-tailing or C-tailing to double-stranded DNA or cDNA. Strand S could have a phosphorothioate bond (*) before the terminal T, ensuring that exonucleases cannot digest the T overhang that pairs to the A-tail added to library fragments. Note that strand S lacks the universal sequence A portion as seen in strand L. With this design, even if adapters are ligated with each other to form adapter-dimer, the adapter-dimer cannot be amplified in the downstream reaction. In the design shown here, the region of strand L paired with strand S also serves as barcode, however the barcode portion could be at a different position in strand L. Panel B depicts the gene-specific primer design, where 5' end of this primer is a universal sequence B, 3' end of this primer is gene-specific. Panel C depicts the orientation of gene-specific primers. A forward primer anneals to the template (−) strand, and is identical to (a part of) the template (+) strand. And a reverse primer anneals to the template (+) strand and is identical to (a part of) the template (−) strand. Forward, reverse, (+) and (−) refer to the published strand of reference genome assembly. Panel D depicts the biotin-labeled common primer A and common primer A without biotin. The nucleotide sequences parts of biotin-labeled common primer A and common primer A without biotin are identical. Panel E depicts the common primer B.

The present disclosure generally relates to methods of multiplex target amplification and target enrichment prior to downstream analysis of amplicons, such as next-generation sequencing (NGS). The present disclosure describes methods and kits for amplification and enrichment of specific targets for determining the nucleotide sequence of such targets. The following examples, applications, descriptions and content are exemplary and explanatory, and are non-limiting and non-restrictive in any way.

As used herein, "cfDNA" means cell-free DNA.
As used herein, "cffDNA" means cell-free fetal DNA.
As used herein, "compatibility score" means a score for a potential forward strand-specific primer or reverse strand-specific primer that is calculated based on different factors of target amplicon GC content, target amplicon melting temperature, target amplicon heterozygosity rate, complementary rate of the candidate primer for the target region; candidate primer size, target amplicon size, primer-primer interactions and amplification efficiency and off-target rate.

As used herein, "CNV" means copy number variation.
As used herein, "ctDNA" means cell-free tumor DNA or circulating tumor DNA.
As used herein, "dsDNA" means double stranded DNA.
As used herein, "FFPE" means formalin-fixed paraffin-embedded.
As used herein, "FNA" means fine needle aspiration.
As used herein, "forward strand" means one strand of a dsDNA sample.
As used herein, "forward strand-specific primer" means a primer configured to bind to a target sequence on the forward strand.
As used herein, "GC content" means guanine-cytosine content.
As used herein, "NGS" means next-generation sequencing.
As used herein, "PCR" means polymerase chain reaction.
As used herein, "reverse strand" means a second strand of a dsDNA sample that is complementary to the forward strand.
As used herein, "reverse strand-specific primer" means a primer configured to bind to a target sequence on the reverse strand.
As used herein, "SNP" means single nucleotide polymorphism.
As used herein, "STR" means short tandem repeat.
As used herein, "strand L" means the long strand of a partially double-stranded blocking adapter.
As used herein, "strand S" means the short strand of a partially double-stranded blocking adapter.
As used herein, "UMI" means unique molecular identifier.
As used herein, "universal sequence" means a sequence configured to be targeted by a common primer.

One of the key elements for successful next-generation sequencing is the ability to successfully enrich for target regions in an unbiased manner, enabling detection of mutations in multiple target genes across a genome. Target enrichment can be performed by hybridization-based methods using two different approaches: the solid phase and in-solution. The solid phase target enrichment uses microarrays. Despite variability among various hybridization methods, drawbacks include the requirement for higher input nucleic acid templates and that they are more time-consuming than PCR-based target enrichment due to time required for probe-hybridization and multiple cleanup steps. Both solid-phase and in-solution hybridization can be influenced by sample base composition. Sequences containing high A-T and G-C content can be missed due to poor annealing and secondary structure formations. Moreover, repetitive elements of the genome can cause biases through uneven coverage as they may comprise a high proportion of the sequencing reads.

Compared to hybridization-based method of enrichment, PCR-based target enrichment methods are faster, require fewer steps and less input DNA, and are more suitable for samples containing low amounts of input DNA such as FFPE, cfDNA and ctDNA. The specificity of PCR for target enrichment of regions of interest is significantly influenced by the number of primers in the reaction, primer characteristics such as G-C content, and presence of variations in target regions, which might interfere with optimal primer hybridization, causing amplification failure of certain sequences also known as allele drop-out. Amplicon size and tiling are important considerations for PCR-based target enrichment in order to generate even and uniform coverage.

The human genome contains approximately 3 billion bases, about 21,000 coding genes and over 220,000 exons. The exons represent around 1-2% of the genome and there are nine exons per gene on an average scale with an average exon size of 170 nucleotides. NGS is an important tool for analyzing the genome, has a higher sensitivity than Sanger sequencing, and allows the detection of mutations from a sample containing just a few cells. It can be utilized to detect multiple sequence variations such as single and multi-nucleotide variants, insertions, deletions and gene copy number variations in DNA and RNA. NGS can also be utilized to analyze gene expression levels by measuring quantitatively the levels of mRNA, microRNA and factors affecting them like gene promoter methylation. NGS is revolutionizing molecular characterization of inherited diseases and cancers both for discovery of driver mutations and routine screening of genomic aberrations. Because of a wide range of different applications, NGS has covered many fields of life sciences and is significantly impacting medical genetics, both in research and diagnostics. Isolating high-priority segments of the genomes immensely enhances the outcome in clinical, diagnostic or research settings. Many studies are designed to identify polymorphisms and genetic variation of protein coding genes in a genome wide approach also known as whole exome sequencing (WES).

Nevertheless, since the majority of known disease-causing mutations occur in the coding region of genes, concentrating the focus on sequence analysis of a panel of genes relevant to a particular disease is more practical. There is a great need to design applications where a focus on specific genomic intervals or gene sets is required. Distinctly, it is more cost-effective and time-efficient to target, capture, and sequence the genomic regions of interest especially in clinical settings, where each target can be analyzed with greater depth and large number of specific gene panels and high sample numbers can be analyzed simultaneously.

While whole genome sequencing is becoming more cost-effective and more practical for many indications, a focused target-specific panel continues to offer the advantages of better coverage of targeted regions, greater facility to detect multiple variant types (including CNVs and complicated genomic rearrangements), substantially lower costs, higher throughput, simpler bioinformatics analysis, and focused testing, obviating the need to deal with secondary/incidental findings that otherwise inevitably arise with whole genome sequencing. Furthermore, targeted sequencing of specific regions of interest in a large number of samples is much more cost-effective in providing answers to biological questions than sequencing the whole genomes of fewer individuals. Wider coverage of specific targets and deeper sequencing of enriched targets allows a broader dynamic range in allele frequencies and detection of minority sequences and low frequency variations for disease evaluation, treatment and prognosis. An efficient and specific target enrichment method allows more efficient targeted sequencing. The important parameters for target enrichment are: (i) sensitivity; (ii) specificity; (iii) uniformity; (iv) reproducibility; (v) cost; (vi) ease of use; and (vii) amount of DNA required per experiment.

Using NGS to focus on particular regions of interest, however, requires enrichment of relevant target regions. Notably, target enrichment allows increased coverage of target regions and specific regions of interest, facilitating multiplexing of samples and simplifying sequence read data analysis. Fundamental advantages of target enrichment in genomic assays include enrichment factor, coverage or read depth, uniformity or evenness of coverage across the target region of interest, reproducibility, specificity that is on-target/off-target ratio of sequence reads, required input DNA amount and overall cost per target base of useful sequence data.

The presently disclosed methods can be used for a variety of applications, including, but not limited to, genotyping, detection of chromosomal abnormalities (such as a fetal chromosome aneuploidy), gene mutation and polymorphism (such as single nucleotide polymorphisms, SNPs) analysis, gene deletion, determination of paternity, analysis of genetic differences among populations, forensic analysis, measuring predisposition to disease, quantitative analysis of mRNA, and detection and identification of infectious agents (such as bacteria, parasite, and viruses). The disclosed methods can also be used for non-invasive prenatal testing, including, but not limited to, paternity testing or the detection of fetal chromosome abnormalities.

Figure 2:
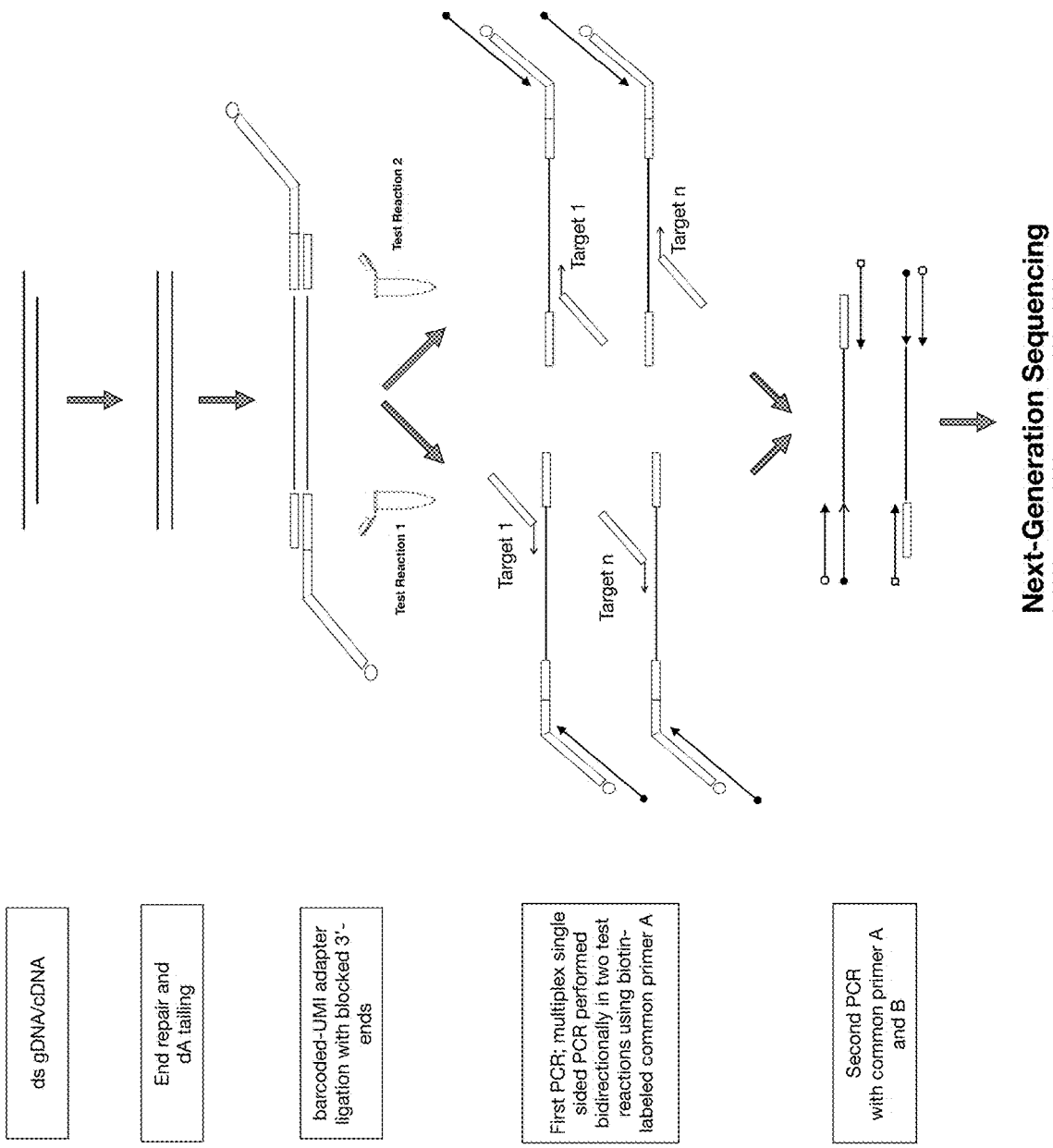
FIG. 2 depicts a schematic drawing of library preparation for DNA sequencing. 1) The fragmented double-stranded genomic DNA or double-stranded cDNA is treated with end repairing and dA-tailing (in case of RNA, RNA needs to be converted to ds cDNA); 2) Partially double-stranded blocking adapter ligation to double-stranded genomic DNA or double-stranded cDNA; 3) First amplification in two separate test reactions with biotin-labeled common primer A and multiplex forward strand-specific primers in one test reaction and biotin-labeled common primer A and multiplex reverse strand-specific primers in another test reaction; 4) The biotin-labeled amplicons are pooled and enriched by streptavidin coated beads (not shown); 5) Second amplification is performed by common primers A and B; 6) the amplified product is analyzed by NGS.
Figure 3:
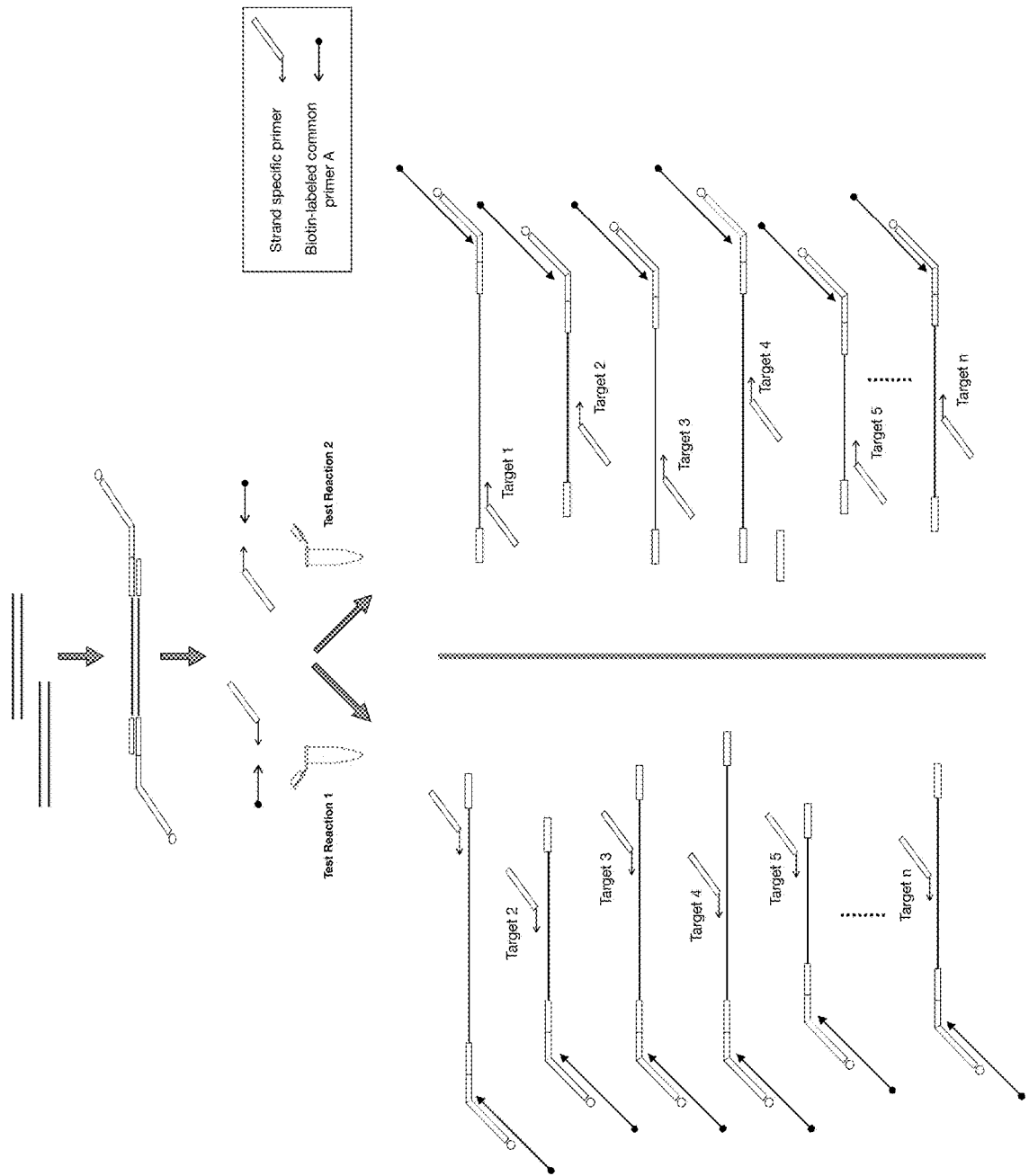
FIG. 3 depicts an illustration of two test reaction multiplex strand-specific amplification approach with forward strand-specific primers and biotin-labeled common primer A in one test reaction and reverse strand-specific primers and biotin-labeled common primer A in a second test reaction (in a separate tube or other reaction chamber), where amplicons of different sizes are generated.
Figure 4:
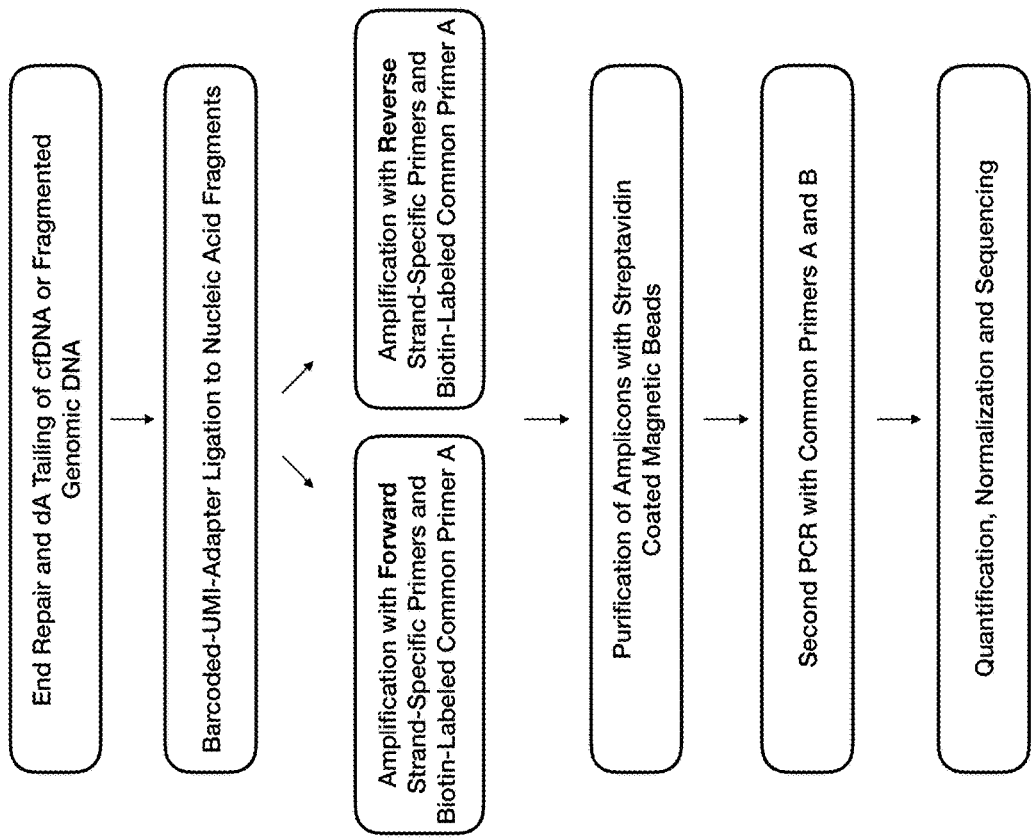
FIG. 4 illustrates the workflow of a genomic DNA or a cell free DNA sample.
Figure 5:
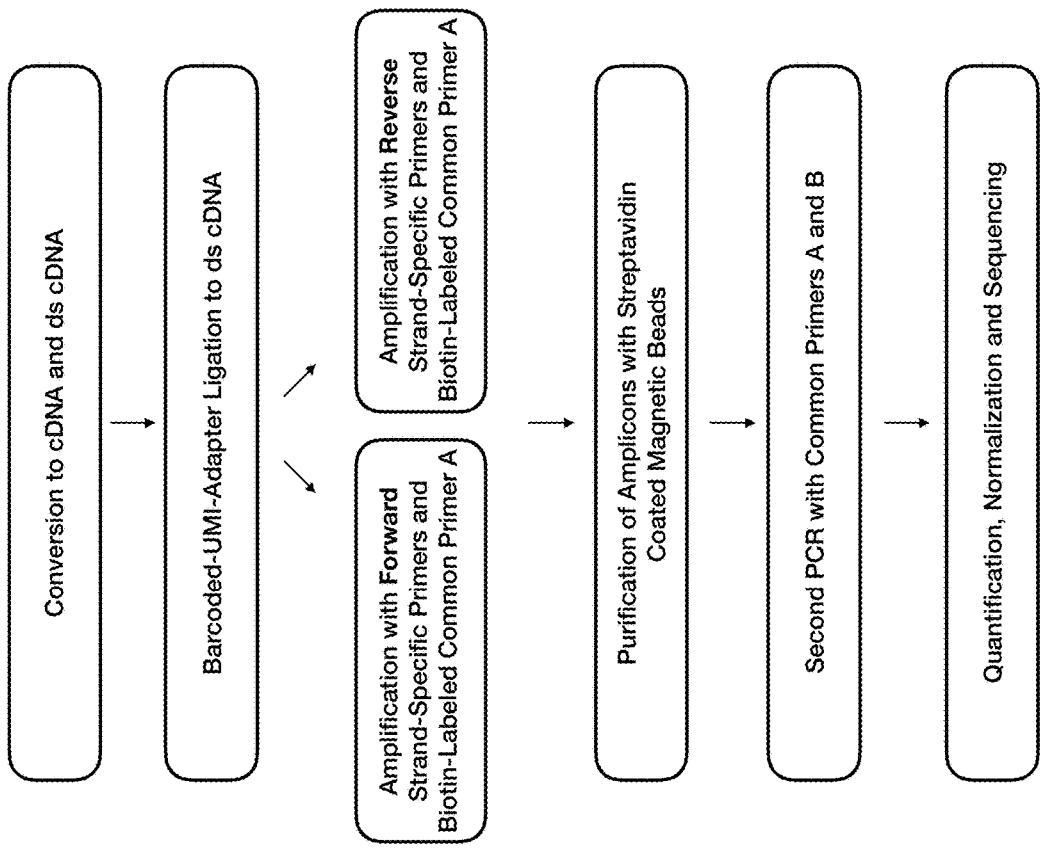
FIG. 5 illustrates the workflow of an RNA sample.

The present disclosure describes methods of multiplex target enrichment for further analysis, such as through NGS. One such method comprises the steps of: end repair and dA tailing of genomic DNA or, in the case of RNA, conversion to double stranded cDNA (see, e.g., FIG. 5); ligation of partially double-stranded blocking adapters to either 5'-end or 3'-end of dsDNA/cDNA fragments or both sides of nucleic acid fragments wherein strand L of partially double-stranded blocking adapters comprise a universal sequence A, a barcode sequence and a UMI (see FIG. 1); amplification of DNA fragments in two test reactions by forward strand-specific primers and a biotin-labeled common primer A in a first test reaction, and reverse strand-specific primers and a biotin-labeled common primer A in a second test reaction resulting in a first set of amplicons; enrichment of the first set of amplicons by binding the amplicons to streptavidin beads; performing a second amplification of the enriched amplicons with common primer A and B to form a final set of amplicons; and sequencing the final set of amplicons by NGS (see, e.g., FIGS. 2 and 3).

The forward strand-specific primers and reverse strand-specific primers may anneal specifically to different regions on a target region, gene or different exons of a gene. Each forward strand-specific primer and reverse strand-specific primer may comprise a universal sequence B and a target-specific sequence (with the target-specific sequence targeting a specific sequence on the forward or reverse strand, respectively).

The 3'-end can be blocked by for ligation or polymerase extension by methods including, but not limited to, by introducing at the 3' end of adapter with modified bases such as inverted dT (FIG. 9. A) can be incorporated at the 3'-end of an oligo, leading to a 3'-3' linkage which inhibits both degradation by 3' exonucleases and extension by DNA polymerases, or y (i.e. dideoxycytidine, ddC FIG. 9. B); or with spacer of different length such as C3 spacer (FIG. 9. C), hexanediol (FIG. 9. D).

A nucleic acid sample to be analyzed may have a plurality of double stranded nucleic acid fragments. The partially double-stranded blocking adapters may be ligated to nucleic acid fragments (double stranded gDNA or cDNA) that are a combination of both target and non-target nucleic acid fragments. The forward strand-specific primers and reverse strand-specific primers may hybridize to target nucleic acid fragments in the sample for amplification.

The partially double-stranded blocking adapters can be ligated using state-of-art approaches such as blunt-end ligation or sticky-end or TA ligation. In some embodiments, the nucleic acid fragments (double stranded gDNA or ds cDNA) can be subjected to phosphorylation and/or adenylation prior to ligation of partially double-stranded blocking adapters.

The method disclosed herein can also be used to quantify the copies of a target sequence of interest that has at least one allele with a deletion by subjecting the amplicons to NGS, analysis and quantification of the resulting sequence data by a software algorithm, counting the amplicons and determining the deletion.

The amplification conditions, such as number of cycles, annealing temperature, annealing duration, extension temperature and extension duration may be adjusted to optimal conditions for amplification. In some embodiments, such amplification conditions may be based on commercial DNA polymerase instructions.

The methods described herein include the advantages of using strand-specific primers in a multi-test reaction amplification solution (i.e., two or more test reactions), which avoids the constraints for primer selection and facilitates assay development, because there is no requirement for primer pairing. In some embodiments, the forward strand-specific primers and reverse strand-specific primers can minimize primer-dimer formations significantly, because there are about 50% fewer primers in the reaction compared to conventional target-specific primer pairs. The UMI introduced in the strand L of partially double-stranded blocking adapter, can be used to quantify the original copies of input nucleic acid fragments, which eliminates amplification and sequencing errors in data analysis.

Using forward strand-specific primers and reverse strand-specific primers provides significant advantages over conventional PCR methods for samples comprising short nucleic acid fragments, such as cell-free DNA (cfDNA). Because cfDNA comprises short nucleic acid fragments of different sizes, the probability of traditional PCR primer pair hybridizing to a short length target nucleic acid decreases; by using strand-specific amplification, each target-specific primer hybridizes to the target nucleic acid on one strand for amplification, the probability of hybridization to short fragments increases significantly as there is no need for primer pairing amplification. The disclosed methods herein also allow amplification of a wide range of short nucleic acid fragments from different cfDNA sample, such as cell-free fetal DNA (cffDNA), cell-free tumor DNA (ctDNA) or formalin-fixed paraffin-embedded (FFPE) DNA or RNA; the short DNA fragment can be less than 40 bases, 50 bases, 60 bases, 70 bases, 80 bases, 90 bases, 100 bases or 120 bases.

Utilization of the described methodology has many advantages: strand-specific amplification can determine accurate gene variations, because forward and reverse strands of double-stranded DNA template are amplified and analyzed in separate reactions (see, e.g., FIG. 6), and during computational data analysis, sequencing reads derived from original forward and reverse strands can be identifiable; through proper design, each variant is covered by at least one forward and one reverse primer and after data analysis, only variants present in reads derived from both original forward strands and reverse strands are considered variants. This procedure significantly eliminates false positive artifacts arising from sample preparation, PCR and sequencing artifacts. Other major advantages of the disclosed methodology include, but are not limited to: 1) where strand L of partially double-stranded blocking adapter has a UMI, it facilitates quantification of the original copies of input nucleic acid fragments and facilitates detection of amplification and sequencing artifacts; 2) The blocking at the 3'-end of the strand L of partially double-stranded blocking adapter prevents strand L of partially double-stranded blocking adapter from being used as a primer in downstream reactions; 3) using the partially double-stranded adapter, even if adapter is ligated with another adapter to form an adapter-dimer, the adapter-dimer cannot be amplified. Therefore, a high concentration of partially double-stranded blocking adapter can be used in ligation reaction, which increases the sensitivity of the entire procedure; 4) in the first amplification, there is a biotin-labeled common primer A that can only hybridize with the strand L of partially double-stranded blocking adapter. Due to the fact that highly multiplex PCR generates artifacts, only fragments amplified with biotin-primer will be enriched for the second round of amplification. This further reduces primer-dimer formation, increases the sensitivity of the test; and 5) strand-specific amplification increases specificity and simplifies multiplex primer design because gene-specific primers don't need to be paired with proper size constraint as in conventional PCR reaction and in addition, almost 50% fewer primers are introduced in a multiplex PCR. Each strand is amplified independently of the other strand, avoiding false positive amplification.

The target nucleic acid sequences can be quantified by counting the sequences. For example, the quantity of control sequences is used as a comparison tool for determining abnormal condition when compared to the quantity of control sequences in a normal region of genome in the same sample. The relative quantity of each of the target nucleic acid sequences can be standardized by the control normal region of the genome. For example, aneuploidy can occur at chromosome 13, chromosome 18, chromosome 21, chromosome X, and chromosome Y, and chromosome 1 can be used as a control region.

In some embodiments, the nucleic acid sample comprises genomic DNA or RNA. In other embodiments, the nucleic acid sample comprises nucleic acid molecules obtained from FFPE or archived DNA samples. In other embodiments, the nucleic acid sample comprises mechanically or enzymatically sheared or fragmented DNA. In some embodiments, the nucleic acid sample comprises circulating cfDNA, such as material obtained from a maternal subject; the nucleic acid sample may comprise ctDNA from an individual with cancer or from an individual for cancer screening purposes. A nucleic acid sample may comprise proteins, cells, fluids, biological fluids, preservatives, and/or other substances. In some embodiments, the nucleic acid sample comprises nucleic acid molecules obtained from blood, serum, plasma, spinal fluid, urine, tissue, saliva, biopsies, sputum, swabs, FFPE, surgical resections, cervical swabs, tears, tumor tissue, FNA, circulating cfDNA, and ctDNA, scrapings, swabs, mucus, urine, semen, hair, laser capture microdissections, and other non-restricting clinical or laboratory obtained samples. In some embodiments, the nucleic acid sample is epidemiological, bacterial, viral, fungal, agricultural, forensic or pathogenic.

In some embodiments, the nucleic acid sample is obtained from an animal, such as a human or other mammal. In other embodiments, the nucleic acid sample is obtained from a non-mammalian subject, such as a bacterium, virus, fungi or plant.

In some embodiments, the disclosure relates to a method of amplification of at least one target sequence from a nucleic acid sample from a normal or diseased subject. In some embodiments, the disclosure relates to the specific and selective amplification of at least one target sequence and detection and identification of mutations in a nucleic acid sample that is indicative of disease. In some embodiments, the detected mutation can be clinically-actionable mutations (i.e., a mutation for which a treatment is known or otherwise available). In some embodiments, detected mutations can be associated with drug resistance or companion diagnostic treatment. In some embodiments, detection, identification and/or quantitation of genetic markers can be related with organ transplantation or organ rejection. In some embodiments, the nucleic acid sample can be screened for inherited disease or cancer. In some embodiments, a nucleic acid sample from a diseased or healthy subject can be whole genomic DNA, mechanically or enzymatically fragmented DNA, cDNA, FFPE, cfDNA or ctDNA.

In some embodiments, the disclosure relates to a method of selective amplification of target sequences wherein mutations of such target sequences are associated with cancer. In some embodiments, the amplified target sequences may be related to head and neck cancers, brain cancer, breast cancer, ovarian cancer, cervical cancer, colorectal cancer, endometrial cancer, gallbladder cancer, gastric cancer, bladder cancer, prostate cancer, testicular cancer, liver cancer, lung cancer, kidney (renal cell) cancer, esophageal cancer, pancreatic cancer, thyroid cancer, bile duct cancer, pituitary tumor, Wilms tumor, Kaposi sarcoma, osteosarcoma, thymus cancer, skin cancer, heart cancer, oral and larynx cancer, leukemia, neuroblastoma and/or non-Hodgkin lymphoma. In some embodiments, the mutations can include substitutions, insertions, inversions, point mutations, deletions, mismatches and translocations. In some embodiments, the mutations can include variation in copy number. In some embodiments, the mutations can include germline or somatic mutations. In some embodiments, the sample can be screened by the disclosed methods for the presence of cancer.

In some embodiments, target strand-specific primers designed for cancer, based on the described primer selection criteria herein, can include: 10; 20; 100; 500; 1,000; 2,500; 5,000; 10,000; 25,000; 50,000; 80,000; 100,000; or 150,000 or greater, target sequence-specific primers.

In some embodiments, the disclosed kit comprises forward strand-specific primers and reverse strand-specific primers that are directed to one or more genes associated with high-prevalence clinically relevant cancer genes covering many cancers. In some embodiments, forward strand-specific primers and reverse strand-specific primers associated with cancer are directed to amplify one or more genes that are clinically relevant for many cancers, including, but not limited to: AIP, ALK, APC, ATM, BAP1, BARD1, BLM, BMPR1A, BRCA1, BRCA2, BRIP1, CDH1, CDK4, CDKN1B, CDKN2A, CHEK2, DICER1, EPCAM, FANCC, FH, FLCN, GALNT12, GREM1, HOXB13, MAX, MEN1, MET, MITF, MLH1, MRE11A, MSH2, MSH6, MUTYH, NBN, NF1, NF2, PALB2, PHOX2B, PMS2, POLD1, POLE, POT1, PRKAR1A, PTCH1, PTEN, RAD50, RAD51C, RAD51D, R131, RET, SDHA, SDHAF2, SDHB, SDHC, SDHD, SMAD4, SMARCA4, SMARCB1, SMARCE1, STK11, SUFU, TMEM127, TP53, TSC1, TSC2, VHL, and XRCC2.

In some embodiments, the disclosed kit comprises forward strand-specific primers and reverse strand-specific primers that are directed to one or more genes associated with breast cancer. In some embodiments, forward strand-specific primers and reverse strand-specific primers associated with breast cancer are directed for amplification of one or more genes, including but not limited to: ATM, BARD1, BRCA1, BRCA2, BRIP1, CDH1, CHEK2, FANCC, MRE11A, MUTYH, NBN, NF1, PALB2, PTEN, RAD50, RAD51C, RAD51D, STK11, and TP53.

In some embodiments, the disclosed kit comprises forward strand-specific primers and reverse strand-specific primers that are directed to one or more genes associated with ovarian cancer. In some embodiments, forward strand-specific primers and reverse strand-specific primers associated with ovarian cancer are directed for amplification of one or more genes, including but not limited to: ATM, BARD1, BRCA1, BRCA2, BRIP1, CDH1, CHEK2, DICER1, EPCAM, MLH1, MRE11A, MSH2, MSH6, MUTYH, NBN, NF1, PALB2, PMS2, PTEN, RAD50, RAD51C, RAD51D, SMARCA4, STK11, and TP53.

In some embodiments, the disclosed kit comprises forward strand-specific primers and reverse strand-specific primers that are directed to one or more genes associated with colorectal cancer. In some embodiments, forward strand-specific primers and reverse strand-specific primers associated with colorectal cancer are directed for amplification of one or more genes, including but not limited to: APC, BMPR1A, CDH1, CHEK2, EPCAM, GREM1, MLH1, MSH2, MSH6, MUTYH, PMS2, POLD1, POLE, PTEN, SMAD4, STK11, and TP53.

In some embodiments, the disclosed kit comprises forward strand-specific primers and reverse strand-specific primers that are directed to one or more genes associated with prostate cancer. In some embodiments, forward strand-specific primers and reverse strand-specific primers associated with prostate cancer are directed for amplification of one or more genes, including but not limited to: ATM, BRCA1, BRCA2, CHEK2, EPCAM, HOXB13, MLH1, MSH2, MSH6, NBN, PALB2, PMS2, RAD51D, and TP53.

In some embodiments, the disclosed kit comprises forward strand-specific primers and reverse strand-specific primers that are directed to detection and identification of fusion genes, such as abnormal gene fusions or transforming gene fusions (e.g., EML4-ALK or ROS1) in cancer. In some embodiments, forward strand-specific primers and reverse strand-specific primers for amplification are directed for detection of one or more fusion genes in cancer, including but not limited to: AKT3, ALK, ARHGAP26, AXL, BRAF, BRD3, BRD4, EGFR, ERG, ESR1, ETV1, ETV4, ETV5, ETV6, EWSR1, FGFR1, FGFR2, FGFR3, FGR, INSR, MAML2, MAST1, MAST2, MET, MSMB, MUSK, MYB, NOTCH1, NOTCH2, NRG1, NTRK1, NTRK2, NTRK3, NUMBL, NUTM1, PDGFRA, PDGFRB, PIK3CA, PKN1, PPARG, PRKCA, PRKCB, RAF1, RELA, RET, ROS1, RSPO2, RSPO3, TERT, TFE3, TFEB, THADA, and TMPRSS2.

In some embodiments, the disclosure relates generally to using target sequence-specific primers to amplify target sequences that may carry mutations associated with a congenital or inherited disease. The mutations can be somatic or germline mutations. In some embodiments, the mutations can be autosomal dominant or autosomal recessive. In some embodiments, the disclosure relates to amplification of target sequences in a nucleic acid sample associated with one or more inherited diseases.

In some embodiments, the mutations associated with a congenital or inherited disease include point mutations, insertions, deletions, inversions, substitutions, mismatches, translocations and/or copy number variations. In some embodiments, the disclosure relates generally to amplification of target sequences that can include mutation(s) associated with an inherited disease.

In some embodiments, the disclosed kit comprises forward strand-specific primers and reverse strand-specific primers that are directed to one or more genes associated with cardiovascular disease. In some embodiments, forward strand-specific primers and reverse strand-specific primers associated with cardiovascular disease are directed for amplification of one or more genes, including but not limited to: ABCC9, ACTA2, ACTC1, ACTN2, AKAP9, ANK2, ANKRD1, BAG3, CACNA1C, CACNA2D1, CACNB2, CALM1, CASQ2, CAV3, CBS, COL3A1, COL5A1, COL5A2, CRYAB, CSRP3, DES, DMD, DSC2, DSG2, DSP, EMD, EYA4, FBN1, FBN2, FKTN, FLNA, FXN, GATA4, GATAD1, GLA, GPD1L, HCN4, JAG1, JPH2, JUP, KCND3, KCNE1, KCNE2, KCNE3, KCNH2, KCNJ2, KCNJ5, KCNJ8, KCNQ1, LAMA4, LAMP2, LDB3, LMNA, MED12, MYBPC3, MYH11, MYH6, MYH7, MYL2, MYL3, MYLK, MYOZ2, MYPN, NEXN, NKX2-5, NOTCH1, PKP2, PLN, PLOD1, PRKAG2, PRKG1, PTPN11, RAF1, RBM20, RYR2, SCN1B, SCN2B, SCN3B, SCN4B, SCN5A, SKI, SLC2A10, SMAD3, SMAD4, SNTA1, TAZ, TBX1, TBX20, TBX5, TCAP, TGFB2, TGFB3, TGFBR1, TGFBR2, TMEM43, TMPO, TNNC1, TNNI3, TNNT2, TPM1, TRDN, TRPM4, TTN, TTR, TXNRD2, and VCL.

In some embodiments, target sequence-specific primers designed for congenital or inherited diseases based on the criteria described herein can include: 10; 20; 100; 500; 1,000; 2,500; 5,000; 10,000; 25,000; 50,000; 80,000; 100,000; or 150,000 or greater forward strand-specific primers or reverse strand-specific primers in a test reaction. In some embodiments, at least one of the target sequence-specific primers associated with an inherited disease is at least 90% identical to the target sequence.

In some embodiments, the disclosure relates generally to the selective amplification of more than one target sequence in a nucleic acid sample and the detection and/or identification of mutations associated with a congenital or inherited disease. In some embodiments, the disclosure relates generally to the amplification of a plurality of target sequences linked to or correlated with a congenital or inherited disease.

In some embodiments, the candidate forward strand-specific primers and reverse strand-specific primers are designed based on mentioned criteria to amplify target nucleic acid sequences that are associated with a congenital or inherited disease. In some embodiments, the forward strand-specific primers and reverse strand-specific primers can contact dsDNA or cDNA fragments and amplify nucleic acid targets that are associated with heredity disorders.

In some embodiments, the disclosure relates to using the forward strand-specific primers and reverse strand-specific primers to screen for newborn disorders. In some embodiments, the disclosure relates to use the candidate forward strand-specific primers and reverse strand-specific primers to detect or screen for newborn disorders by contacting target sequences in a nucleic acid sample and amplifying the target sequence regions for detecting newborn disorders. In some embodiments, the forward strand-specific primers and reverse strand-specific primers contact many target sequences in a multiplex fashion and can detect at least one or more newborn disorders. The present disclosure also discloses a kit for newborn screening based on a plurality of forward strand-specific primers and reverse strand-specific primers that can detect at least one or more newborn disorders.

In some embodiments, the disclosure relates to using forward strand-specific primers and reverse strand-specific primers for forensic testing. In some embodiments, the origin of the nucleic acid sample can be blood, hair, biopsy, body fluids and other material that contain biological DNA. In some embodiments, the forward strand-specific primers and reverse strand-specific primers can hybridize to STRs of target nucleic acids, which is state-of-art for human identification.

In some embodiments, the presently disclosed methods comprise the use of forward strand-specific primers and reverse strand-specific primers that hybridize to target sequences on a DNA strand, wherein increasing specificity as well as simplifying and streamlining multiplex primer design because gene-specific primers in the same amplification reaction will not allow amplification of off-target regions by design and in addition, almost 50% less primers are introduced in a multiplex PCR; each strand is amplified independently of the other strand, avoiding false positive amplification.

In some embodiments, the forward strand-specific primers and reverse strand-specific primers include a plurality of primers that are selectively designed to amplify target sequences; the amplification range differs due to the size of fragments and positions of primers on the nucleic acid fragment and the size can vary in the range of about 50 base pairs to about 1,000 base pairs in length. In another embodiment, size selection is performed to enrich for the desired size for sequencing; size selection is performed by application as an example, for ctDNA and cfDNA smaller size nucleic acid fragments are more suitable. In some embodiments, the forward strand-specific primers and reverse strand-specific primers include a plurality of primers that are selectively designed to amplify target sequences, where the amplified target sequences can vary in length from one another by no more than 90%, no more than 70%, no more than 50%, no more than 25% or no more than 10%.

The disclosed methods may be used for target sequence enrichment by multiplex strand-specific PCR, which comprises the steps of contacting the nucleic acid targets with a plurality of strand-specific primers (forward strand-specific primers in at least one test reaction and reverse strand-specific primers in at least one other test reaction) and biotin-labeled common primer A in the presence of PCR reagents such as DNA polymerase, dNTPs and reaction buffer; given the optimal conditions of temperature and time for denaturation, annealing and extension, the primers hybridize to complementary target sequences and are extended. In some embodiments, the amplification steps can be performed in any order. In some embodiments, amplification steps, purification steps and cleanup steps could be added or removed upon optimization for optimal multiplex target amplification for downstream processes.

The present disclosure features a broad range of applications in clinical and research settings and can be used for mutation detection and analysis, SNPs, microbial and viral detection, deletions and insertions, genotyping, CNVs, epigenetic and methylation analysis, gene expression, transcriptome analysis, low frequency allele mutations and etc. In some embodiments, the applications can be used for detection, diagnostics, prognosis and treatment of disease. In some embodiments, the mutations can be detected in less than about 10% allele frequency. In some embodiments, the mutations can be detected in less than about 5%, 3%, 1%, 0.5%, 0.1% or 0.01% allele frequency. In some embodiments, the methods described herein can detect both germline and somatic mutations in the amplicons.

In some embodiments, the described method uses PCR and DNA polymerase. In some embodiments, there are a wide selection of DNA polymerases, which feature different characteristics such as thermostability, high-fidelity, processivity and Hot Start. The method can use a DNA polymerase with one or more of these features depending on the application. In some embodiments, the concentration of DNA polymerase for multiplex PCR can be higher than singleplex PCR.

In some embodiments, the method disclosed herein includes partially double-stranded blocking adapters configured to ligate to double-stranded nucleic acid fragments. In some embodiments, strand L of partially double-stranded blocking adapter comprises a universal sequence that is non-complementary to target sequences, a barcode sequence and a UMI. In some embodiments, strand L of partially double-stranded blocking adapter is blocked at 3'-end, which prevents it from being used as a primer in downstream reactions; in addition, with partially double-stranded adapter, even if adapter-dimer formed in ligation reaction, the adapter-dimer cannot be amplified; thus, a high concentration of partially double-stranded adapters can be used in the ligation reaction to increase the sensitivity of the entire procedure. The barcode sequence allows tagging of the nucleic acid fragments from each subject for multiplex detection and can discriminate the identity of multiple samples from different subjects. Barcoding allows increasing the throughput by pooling samples. The UMI serves to reduce the quantitative biases and allows elimination of amplification and sequencing artifacts. In some embodiments, the barcode contains a unique nucleic acid sequence for each subject, commonly 6 to 20 bases to uniquely distinguish amplified fragment identities in multiplex amplification. In some embodiments, the universal sequence on long strand of partially double-stranded blocking adapters or on forward strand-specific primers or reverse strand-specific primers allows uniform amplification of target sequences with reduced bias.

In some embodiments, the common primer A includes a biotin label on the 5'-end in the first PCR reaction, which allows for enrichment of amplicons from the first PCR reaction (first amplification) to reduce amplification biases for the second PCR reaction (second amplification). In some embodiments, in the first amplification, the biotin-labeled common primer A can only hybridize and be extended to a long strand of partially double-stranded blocking adapter; due to the fact that highly multiplex PCR generates artifacts, only fragments amplified with biotin-primer will be enriched for the second amplification, reducing primer-dimer formation and increasing the sensitivity of the method.

In some embodiments, the method disclosed herein uses amplification of target sequences using multiplex polymerase chain reaction, wherein more than one target sequence is amplified in a test reaction. In some embodiments, the amount of nucleic acid sample needed for multiplex amplification can be about 1 ng. In some embodiments, the amount of nucleic acid material can be about 5 ng, 10 ng, 50 ng, 100 ng or 200 ng.

PCR is performed using a thermocycler and each cycle of PCR comprises the steps of denaturation, annealing and extension. Each cycle of PCR includes at least one denaturation step, one annealing step and one extension step for extension of nucleic acids. In some embodiments, annealing and extension can be merged. In some embodiments, the method disclosed herein comprises 5 to 20 cycles of PCR in each round of PCR. Each cycle or set of cycles can have different durations and temperatures, for example the annealing step can have incremental increases and decreases in temperature and duration or the extension step can have incremental increases and decreases in temperature and duration. In some embodiments, duration can have decreases or increases in 5 seconds, 10 seconds, 30 seconds, 1 minute, 2 minutes, 4 minutes, 8 minutes or greater increments. In some embodiments, temperature can have decreases or increases in 0.5, 1, 2, 4, 8, or 10 Celsius increments. In various embodiments, annealing time can be greater than 0.5, 1, 2, 5, 8, 10 or 15 minutes. In various embodiments, extension time can be greater than 0.5, 1, 2, 5, 8, 10 or 15 minutes.

Forward strand-specific primers and reverse strand-specific primers may comprise a nucleotide modification in the 3'-end or 5'-end or across the sequence. The length of target-specific portion of the forward strand-specific primer or reverse strand-specific primer can be about 15 to 40 bases. The $T_m$ of each forward strand-specific primer and reverse strand-specific primer can be about 55° C. to about 72° C.

In some embodiments, the forward strand-specific primers and reverse strand-specific primers contact and hybridize to target sequences that may carry mutations related to disease. In some embodiments, the disease can be cancer or hereditary disease. In some embodiments, the amplicons can be different random sizes due to random sizes of nucleic acid fragments. In some embodiments, forward strand-specific primers and/or reverse strand-specific primers and common primers hybridize to target sequences and the universal sequence, respectively, in each test reaction (as opposed to conventional primer pairs), which leads to amplicons of different sizes. In some embodiments, amplicon size selection can be used to sequence amplicons of a certain length range. In some embodiments, amplicons of about 100 to 250 base pairs range in length can be sequenced. In some embodiments, amplicons of about 150 to 300 base pairs, or amplicons of about 120 to 350 base pairs, or amplicons of about 200 to 500 base pairs range or greater length range can be sequenced.

In some embodiments, the method disclosed herein uses ligation of partially double-stranded blocking adapters for purpose of amplification of a large number of nucleic acid sequences. In some embodiments, the process of ligation and downstream process can include subjecting the nucleic acid fragments to phosphorylation, adapter ligation, nick-translation, amplification and sequencing. In some embodiments, any of the aforementioned procedures can be removed or can be repeated. In some embodiments, purification steps can be added for generating optimal results. These procedures are non-limiting and a skilled person of the art can readily add, remove or repeat the steps for optimal results.

Figure 7:
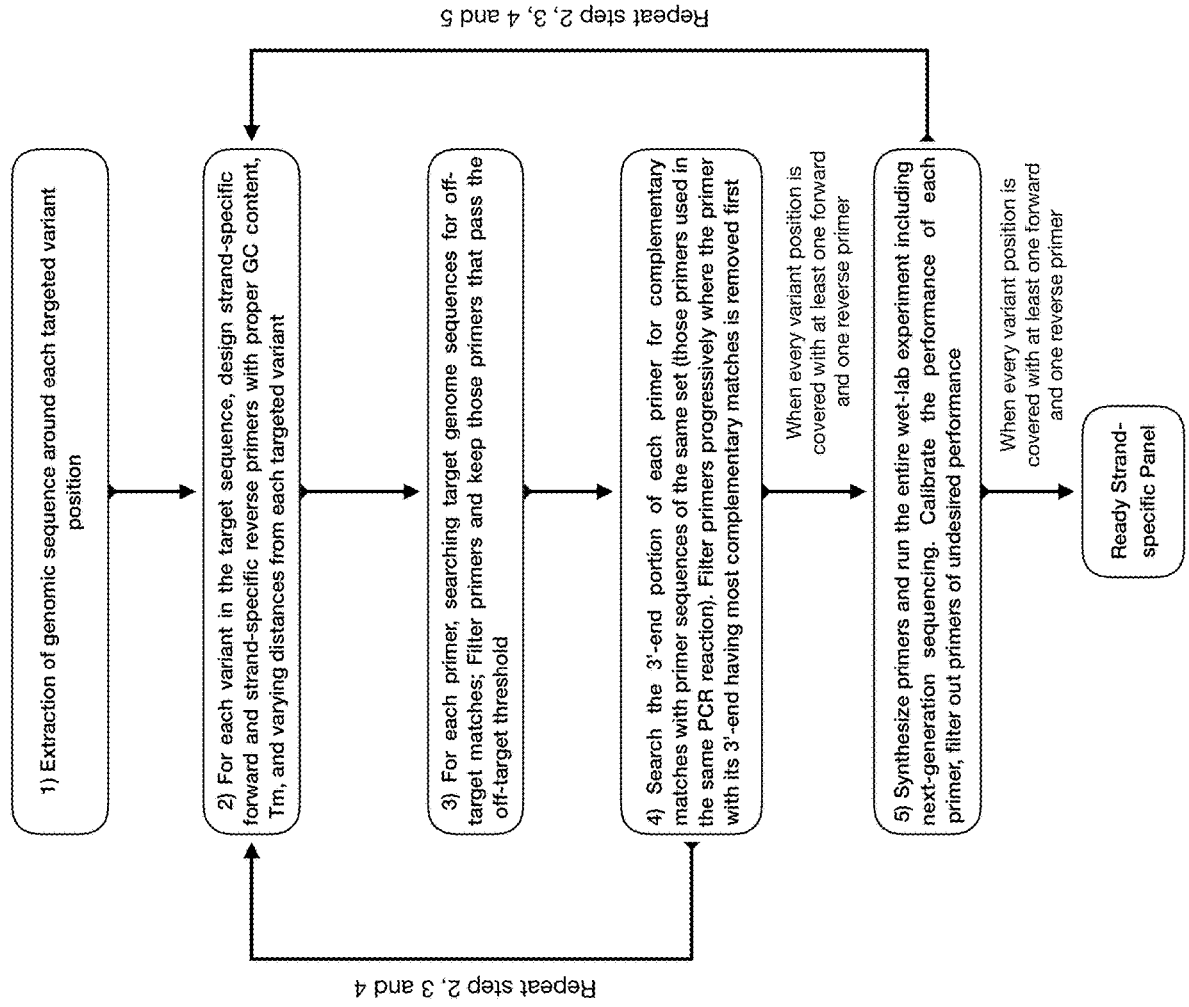
FIG. 7 illustrates the primer design and selection algorithm in a stepwise manner.

The disclosure features utilizing forward strand-specific primers and reverse strand-specific primers for strand-specific amplification of target sequences. Strand-specific amplification has the significant advantages of a more facile and less stringent primer design, more optimal primer selection and less primer-primer interactions, enabling increase of primer numbers in a test reaction. Typically, a small number of primers in a primer set or primer pool cause amplification artifacts such as primer-dimers in multiplex amplification reactions. By employing a primer selection algorithm that can calculate the undesired primer-primer interactions, primer selections can be performed in an efficient manner (see, e.g. FIG. 7). By significantly minimizing primer-primer interactions to a negligible amount, multiplex amplification can simultaneously amplify a large number of target sequences in a single test reaction for each strand. This allows an increase in specific amplification of target sequences while primer-primer interactions reach to a minimum level due to the fact that primers hybridize specifically to target sequences instead of interacting with one another. In some embodiments, one approach for improved specific target sequence amplification is use of lower concentrations of primers and/or increased annealing duration to allow specific hybridization to target nucleic acid sequences than hybridizing to one another and forming primer-dimers.

In some embodiments, the primer design algorithm selects the candidate forward strand-specific primers and reverse strand-specific primers based on this stepwise procedure (FIG. 7): 1) extraction of genomic sequence around each targeted variant position; 2) for each variant in the target sequence, design forward strand-specific and reverse strand-specific primers with proper GC content, $T_m$, and varying distances from each targeted variant; 3) for each primer, searching target genome sequences for off-target matches; filter primers and keep those primers that pass the off-target threshold; 4) search the 3'-end of each primer for complementary matches with primer sequences of the same set (those primers used in the same strand-specific PCR reaction); filter primers progressively where the primer with its 3'-end having most complementary matches is removed first; 5) synthesize primers and run the entire wet-lab experiment including NGS; calibrate the performance of each primer and filter out primers of undesired performance. In some embodiments, the primer selection procedure steps 2 to 4 and steps 2 to 5 are repeated until each target variant is covered by at least one forward primer for forward primer set and one reverse primer for reverse primer set.

In some embodiments, the disclosure features a primer design algorithm that eliminates low compatibility primers that form artifacts such as primer-dimers in a highly multiplexed PCR that inhibit efficient amplification. Such elimination system removes or significantly minimizes the non-productive artifacts such as primer-dimers. Removal of low-compatibility and problematic primers significantly improves the overall performance and efficiency of highly multiplex PCRs in addition to downstream processes such as high throughput sequencing. Artifacts and primer-dimers cause significant failure in obtaining optimal sequence results and can result in a significant portion of the sequencing reads being off-target and non-informative. In detection methods such as microarrays and real-time PCRs that use probes for detection, primer-dimers do not affect the end results significantly as opposed to sequencing.

The ability to increase the number of forward strand-specific primers and reverse strand-specific primers in a multiplex PCR allows simultaneous amplification of a large number (thousands) of target sequences while decreasing the amount of input DNA, labor and time. This is especially advantageous when the amount of starting input nucleic acid material is limited, or the sample is nucleic acid from a single cell.

In some embodiments, the primer selection algorithm features a primer compatibility score both in regard to primer-primer interactions and specific target nucleic acid hybridization without off-target priming or hybridizing to off-target regions. A higher compatibility score for a candidate strand-specific primer characterizes specific hybridization to target nucleic acid with no or minimal interaction with other primers in the primer set. Primers that do not meet the compatibility score that is to say are above the minimum threshold are removed. In various embodiments of the disclosed method, a compatibility score is calculated for at least 80, 90, 95, 98, 99, or 99.5% of the possible combinations of candidate primers in the set. The compatibility score in primer selection is calculated based on a number of parameters such as target amplicon GC content, target amplicon melting temperature, target amplicon heterozygosity rate, complementary rate of the candidate primer for the target region; candidate primer size, target amplicon size and amplification efficiency. Due to the fact that several aspects are involved in determining the compatibility score, an average score is calculated based on multiple parameters and average score could be variable for particular applications. The primer selection algorithm will keep eliminating the low-compatibility primers, and the elimination process is repeated to equal or below minimum threshold till an optimal selection primer group is achieved that generates a highly multiplex target amplification PCR with no or minimized primer-dimers.

In some embodiments, the primer selection algorithm features a primer compatibility score both in regard to primer-primer interactions and specific target sequence hybridization without hybridizing to off-target regions. The primers that have low compatibility score, that is to say above a minimum threshold, will be eliminated. However, if there are limitations in primer selection in certain applications, the minimum threshold can be increased to a higher level of second threshold to facilitate primer selection for the primer group. In some embodiments the selection process is repeated until candidate primers are selected that are equal or under the second level of minimum threshold.

In one embodiment, the disclosed method performs multiplex amplification and target enrichment by utilizing forward strand-specific primers and reverse strand-specific primers that contact target sequences wherein primer-dimers can be reduced or minimized by adjusting different parameters such as duration of annealing steps, increase or decrease of temperature increments, and number of cycles. In some embodiments, the primer concentrations can be lowered, and annealing temperature and duration can be increased to allow specific amplification (the primers have more time interval to hybridize to target nucleic acids) in addition to reduced or minimal primer-dimers. In some embodiments, the concentration of primers can be 500 nM, 250 nM, 100 nM, 80 nM, 70 nM, 50 nM, 30 nM, 10 nM, 2 nM, 1 nM or lower than 1 nM. In some embodiments, the annealing temperature could be 1 minutes, 3 minutes, 5 minutes, 8 minutes, 10 minutes or longer. In some embodiments, the amplification with longer annealing time uses 1 cycle, 2 cycles, 3 cycles, 5 cycles, 8 cycles, 10 cycles or more followed by standard annealing durations.

In one aspect, the present disclosure describes methods of amplifying selective target regions in a nucleic acid sample. In some embodiments, the method includes contacting the nucleic acid sample with forward strand-specific primers in at least one test reaction and reverse strand-specific primers in at least another test reaction, and amplifying at least: 10; 20; 100; 500; 1,000; 2,500; 5,000; 10,000; 25,000; 50,000; 80,000; 100,000; or 150,000 different target regions. In some embodiments, the method also includes determining the presence or absence of at least one target amplification product, for example 50, 60, 70, 80, 90, 95, 99, 95 or 99.5% of the target amplicons. In some embodiments, the method includes determining the sequence of at least one target sequence, for example 50, 60, 70, 80, 90, 95, 99, 95 or 99.5% of the target amplification products. In some embodiments, less than 50, 40, 30, 20, 10, 5, 0.5, or 0.1% of the amplicons are primer-dimers or artifacts. In various embodiments, the primer set or primer pool includes at least: 10; 20; 100; 500; 1,000; 2,500; 5,000; 10,000; 25,000; 50,000; 80,000; 100,000; or 150,000 forward strand-specific primers in a least one test reaction and at least: 10; 20; 100; 500; 1,000; 2,500; 5,000; 10,000; 25,000; 50,000; 80,000; 100, 000; or 150,000 reverse strand-specific primers in at least one other test reaction, wherein each primer is directed to hybridize to a specific target sequence. In some embodiments, there can be more than one set of forward strand-specific primers and more than one set of reverse strand-specific primers as an example there can be two sets of forward strand-specific primers for two test reactions, 3 sets for 3 test reactions or 5 sets for 5 test reactions or more, and there can be two sets of reverse strand-specific primers for two test reactions, 3 sets for 3 test reactions or 5 sets for 5 test reactions or more. In some embodiments for practical reasons such limitations in primer design or selection, the sample may also be split into multiple parallel multiplex test reactions with multiple sets of forward strand-specific primers and the sample may also be split into multiple parallel multiplex test reactions with multiple sets of reverse strand-specific primers.

Variable primer concentrations can be used for different applications of the disclosed method herein. In various embodiments, concentration of each primer can be 500 nM, 250 nM, 100 nM, 80 nM, 70 nM, 50 nM, 30 nM, 10 nM, 2 nM, 1 nM or lower than 1 nM. In various embodiments, primer concentration of each primer can be between 1 µM and 1 nM, between 1 nM and 80 nM, between 1 nM and 100 nM, between 10 nM and 50 nM or 1 nM and 60 nM. In some embodiments, the GC content of strand-specific primers can be between 40% and 70%, or between 30% and 60% or 50% and 80% or 30 and 80%. In some embodiments, primer GC content range can be less 20%, 15%, 10% or 5%. In some embodiments, the $T_m$ of the strand-specific primers can be between 55° C. and 65° C., or 40° C. and 72° C., or 50° C. and 68° C. In some embodiments, the melting temperature range of the primers can be less 20° C., 15° C., 10° C., 5° C., 2° C. or 1° C. In some embodiments, the length of the strand-specific primers can be between 20 and 90 bases, 40 and 70 bases, 20 and 40 bases or 25 and 50 bases. In some embodiments, the range of length of the primers can be 60, 50, 40, 30, 20, 10, 5 bases. In some embodiments, the 5'-region of the forward strand-specific primer and/or reverse strand-specific primer is a universal sequence that are not complementary or specific for any target sequences. In some embodiments, the length of the target amplicons is between 50 and 500 bases, 90 and 350 bases, or 200 and 450 bases.

In one aspect, the present disclosure features a kit that includes target specific single primers in a group. In some embodiments, the kit contains a plurality of forward target strand-specific primers in one group and reverse target strand-specific primers in another group; the primers are designed and selected based on criteria described to have no or minimal primer-primer interactions or off-target priming. In another embodiment, the kit can be formulated for detection, diagnosis, prognosis and treatment of disease such as cancer or congenital or inherited disease. In another embodiment, the kit can be formulated for ploidy status of a gestating fetus for example analyze chromosomes that are associated with trisomy in fetus such as chromosomes 13, 18, 21, X and Y, or some combination thereof. In some embodiments, the kit contains instructions for using the single strand target primers.

In some embodiments, the method may comprise the steps of (1) extracting DNA from the sample such as FFPE or blood or plasma DNA, (2) mechanically or enzymatically fragmentation (3) library preparation with partially double-stranded blocking adapters, (4) amplifying the nucleic acid target by forward strand-specific primers and biotin-labeled common primer A specific to strand L of the partially double-stranded blocking adapter in one test reaction and reverse strand-specific primers and biotin-labeled common primer A specific to strand L of the partially double-stranded blocking adapter in a second test reaction, (5) enrichment of biotin-labeled amplifications with streptavidin beads, (6) second round of PCR with common primers A and B, (7) pooling the samples from different subjects and adjusting the concentration, and (8) sequencing the sample(s). The workflow may include other sub-steps such as purifications. The steps of the method may be performed in different orders.

In some embodiments, the number of forward strand-specific primers or reverse strand-specific primers in a test reaction can be: 10; 20; 100; 500; 1,000; 2,500; 5,000; 10,000; 25,000; 50,000; 80,000; 100,000; or 150,000 or greater, and the target sequences that can be amplified and enriched in a test reaction can be: 10; 20; 100; 500; 1,000; 2,500; 5,000; 10,000; 25,000; 50,000; 80,000; 100,000; or 150,000 or greater. In some embodiments, the method or kit can determine the presence or absence of at least one target sequence such as least 40%, 50%, 60%, 70%, 80%, 90%, 95%, or 99.5% target sequences. In some embodiments, the method disclosed herein can determine the sequence of at least one target amplified product such as 40%, 50%, 60%, 70%, 80%, 90%, 95%, or 99.5% target amplified products. In some embodiments, less than 50, 40, 30, 20, 10, 5, 0.5, or 0.1% of the amplified products are primer-dimers or artifacts. In some embodiments, the kit comprising of a plurality of target-specific single specific primers that at least one target-specific primer is at least 90% identical to any one of the target sequences. In some embodiments, the kit comprising of a plurality of forward strand-specific primers and reverse strand-specific primers can include a sequence identity of at least 91%, 92%, 93%, 94%, 95%, 96%, 97%, 98% or 99% to the target sequences in the nucleic acid sample.

In traditional multiplex PCR, for efficient amplification of short nucleic acid fragments such as cell-free DNA, a primer pair should hybridize to both ends of the small fragment, which has lower probability due to the small size of the nucleic acid. In some embodiments, the forward strand-specific primers and reverse strand-specific primers can be used for efficient amplification of short nucleic acid fragments due to the fact that only one strand-specific primer hybridizes to the short fragment which has significantly higher probability for hybridization. In some embodiments, the forward strand-specific primers and reverse strand-specific primers can efficiently amplify shorter target nucleic acid sequences such nucleic acids derived from FFPE samples, or cfDNA or ctDNA and cffDNA. In some embodiments, the short DNA fragment can be less than 40 bases, 50 bases, 60 bases, 70 bases, 80 bases, 90 bases, 100 bases or 120 bases.

In some embodiments, the methods disclosed herein can be used for detection and quantification of minority mutations lower than 1% such as T790M mutation related to drug resistance in lung cancer.

The methods and kits disclosed herein may use or comprise partially double-stranded blocking adapters where strand L comprise a universal sequence configured for amplification by common primer A. In some embodiments, strand L of partially double-stranded blocking adapters comprise a universal sequence and a blocking 3'-end, a barcode sequence and a UMI; the partially double-stranded blocking adapters are ligated to nucleic acid fragments through standard procedures known to those of skill in the art. In some embodiments, sheared nucleic acid fragments can be blunt-ended by end repair, and dA tailing may add a nucleotide A to the 3' end. The partially double-stranded blocking adapters can be a T-overhang for ligation.

In one aspect, highly multiplex PCR is utilized for the method disclosed. In some embodiments, between 1 and 10 cycles of PCR can be performed for each round of PCR; in some embodiments between 1 and 15 cycles or between 1 and 20 cycles or between 1 and 25 cycles or between 1 and 30 cycles or more can be performed.

In some embodiments, the amplicons can be sequenced by NGS platforms. NGS is referred to non-Sanger based massively parallel DNA nucleic acid sequencing technologies that can sequence millions to billions of DNA strands in parallel. Examples of current state of state-of-art NGS technologies and platforms are Illumina platforms (reversible dye-terminator sequencing), 454 pyrosequencing, Ion Semiconductor sequencing (Ion Torrent), PacBio SMRT sequencing, Qiagen GeneReader sequencing technology, and Oxford Nanopore sequencing. The present disclosure is not limited to these NGS technologies examples.

In another embodiment, the disclosed methods can be used in a multiplex fashion when amplifying more than two target sequences, and the disclosed methods are not limited to any number of multiplexing.

EXAMPLE

Cancer Gene Panel for Identification of Mutations and Fusion Genes in Human Genome Materials and Methods Human genome DNA was used for this experiment to analyze possible mutations that can affect the treatment regimen.

The DNA was extracted by Qiagen FFPE DNA extraction kit according to the manufacturer's instructions and the quantity of DNA was measured both by NanoDrop (ThermoFisher) and Qubit 3 (ThermoFisher).

Input sample of 100 ng of extracted human DNA was sheared with dsDNA Fragmentase (NEB, MA, USA) for 10 minutes to produce average random fragments of about 1 kb. The procedure was performed according to manufacturer's instructions.

The fragmented DNA was purified and then end-repaired by using NEBNext Ultra End Repair/dA-Tailing kit (NEB, MA) following partially double-stranded blocking adapters ligation using NEBNext Ultra II Ligation kit (NEB, MA) according to manufacturer's instructions. The procedures were performed on an Applied Biosystems Veriti thermal cycler (ThermoFisher).

The ligated DNA products were purified by SPRIselect beads (1:1 ratio) to remove surplus partially double-stranded blocking adapters. The end product was eluted in TE buffer.

The strand-specific primer panel was designed for these gene and target mutations. For this panel, 327 primers were designed for multiplex amplification of target nucleic acid sequences.

Cancer genes: AKT1, ALK, BRAF, CTNNB1, EGFR, ERBB2, HRAS, KIT, KRAS, MAP2K1, MET, NRAS, PDGFRA, PIK3CA and TP53.

Microsatellite instability mutations: BAT25, BAT26, MON027, NR21, NR24, NR27.

Fusion genes: ALK, RET, ROS1, NTRK1.

Pharmacogenetic mutations: ABCB1, ABCC2, ABCC4, ACYP2, C8orf34, CBR3, CDA, CYP19A1, CYP2B6, CYP2D6, DHFR, DPYD, DYNC2H1, EGF, ERCC1, FCGR2A, FCGR3A, FOLR3, GGH, GSTM1, GSTP1, GSTT1, MTHFR, MTRR, MTR, NQO1, NT5C2, SEMA3C, SLC19A1, SLC22A16, SLC28A3, SOD2, TP53, TYMS, UGT1A1, UGT1A9, UMPS, XPC and XRCC1.

First round of multiplex strand-specific PCR: In the first round of PCR, two parallel multiplex PCR was performed in two separate reaction tubes. In the first tube, a set of 189 forward strand-specific primers and biotin-labeled common primer A were used with the partially double-stranded blocking adapter ligated nucleic acid template. In the second tube, a set of 138 reverse strand-specific primers and biotin-labeled common primer A were used with the partially double-stranded blocking adapter ligated nucleic acid template. Both reactions were amplified in presence of DNA polymerase, dNTP and PCR buffer. The PCR conditions comprised initiation at 98° C. for 30S, 10 cycles of 98° C. 10S, 67° C. 4 min, 72° C. 1 min and final extension at 72° C. 5 min.

Biotin-labeled PCR products generated from the first round of PCR were purified using Dynabeads™ Streptavidin T1 magnetic beads (Invitrogen). The purified amplicons were used for the second round of PCR.

The second round of PCR was performed using the purified PCR product from the first PCR reaction as a template and common primers A and B. The PCR conditions comprised initiation at 98° C. for 30S, 18 cycles of 98° C. 10S, 68° C. 20S, 72° C. 40S and final extension at 72° C. 2 min. A range of different sizes of amplification products were generated.

The concentration of the amplified products was measured on a Qubit 3 and the amplicon concentrations were normalized and pooled according to Illumina sequencing instructions.

Sequencing of the libraries were performed on a MiniSeq sequencing system (Illumina, CA, USA) using MiniSeq Mid Output Kit.

Figure 8:
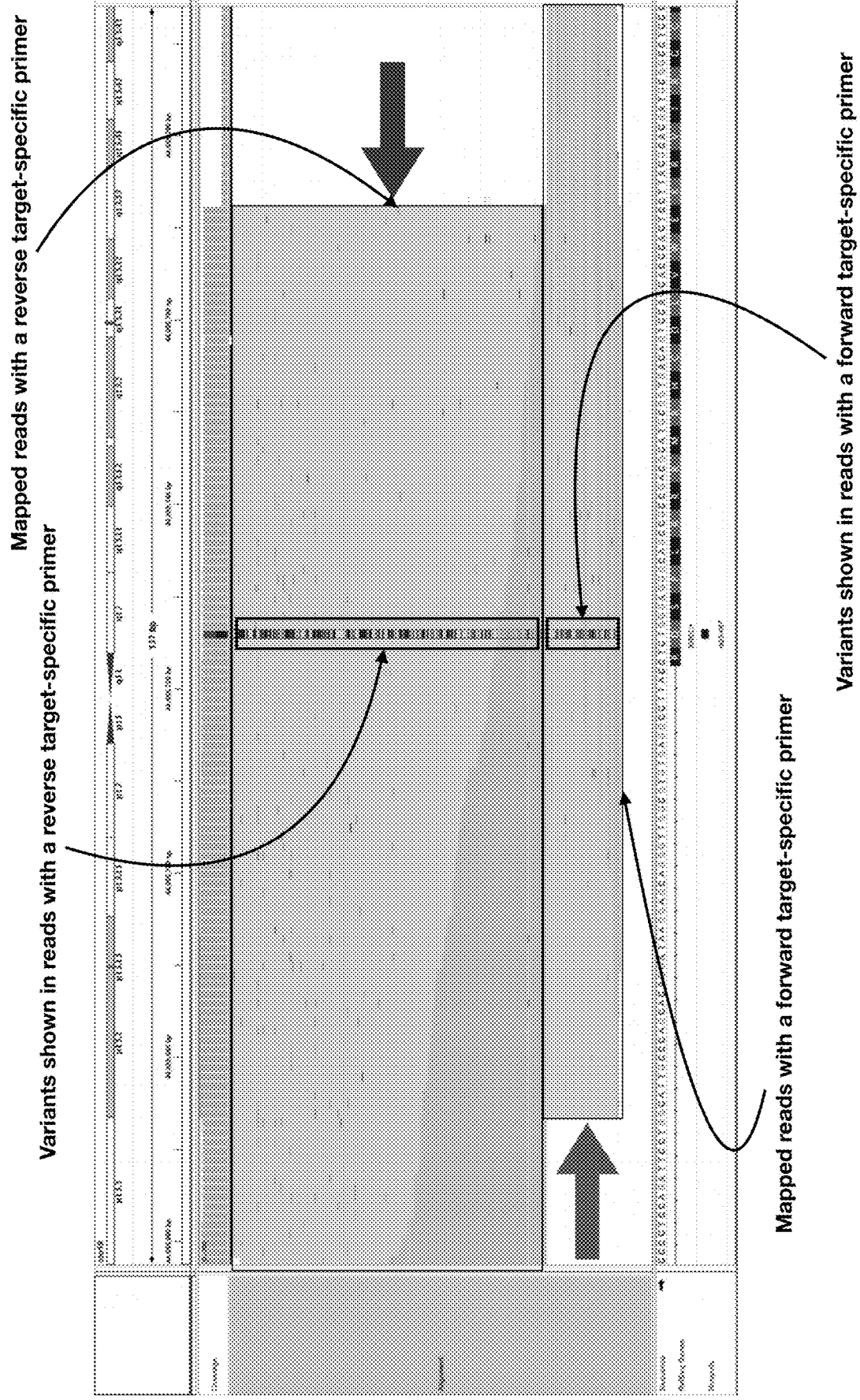
FIG. 8 shows Illumina sequencing reads mapped onto human genomic sequence at chromosome 19 around 44,055, 720 bp, around the SNP rs25487. Reads from PCR reaction with reverse target strand-specific primer are placed on top and reads from PCR reaction with forward target strand-specific primer are displayed at the bottom of the figure. The SNP rs25487 with C/T alleles are shown in both forward and reverse reads, which were derived from two independent PCR reaction with different strands of the double-strand DNA as the template during PCR reaction. This is to demonstrate the usage of the disclosed method generates high genotype with much higher accuracy than conventional methods.

The sequence data generated for the sequence experiment was analyzed for mutations and variations. FIG. 8 shows an example sequence result for SNP rs25487 also known for Gln399Arg located in the DNA repair gene XRCC1. The variations expected in SNP rs25487 are (T:T), (T:C) and (C:C). The SNP rs25487 genotype for this sample is (T:C) and this is truly and accurately confirmed by forward strand-specific and reverse strand-specific sequence results. This example shows the chances for artifact or ambiguity will be minimal once the forward and reverse strand-specific approach is used in two parallel test reactions.

The methods disclosed herein provide significant benefits compared with conventional multiplex amplification methodologies. Conventional methods suffer from amplification artifacts, such as primer-dimers and off-target amplification products, and require primer grouping. The presently disclosed methods, in contrast, relate to an efficient target enrichment approach with high specificity and uniformity that is user-friendly and cost-effective and has a broad range of applications in detection of variations, rearrangements and allele counting. The disclosed methods enable amplification-based target enrichment of a significant number of target-specific sequences with minimal amplification artifacts, such as primer-dimers and off-target amplification products, as well as eliminating or minimizing primer grouping for separate test reactions, which would otherwise necessitate additional steps compared to a single multiplex reaction. In addition, the independent genotyping enabled by amplification (and subsequent sequencing) using forward and reverse primers in separate test reactions allows greater accuracy by one result confirming the other (see, e.g., FIG. 8).

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

Now, therefore, the following is claimed:

1. A method for enrichment of target nucleic acid sequences, comprising the steps of:
   directionally ligating partially double-stranded blocking adapters to the ends of one or more nucleic acid samples;
   combining a portion of the ligated nucleic acid samples with a biotin-labeled common primer A and one or more forward strand-specific primers in one test reaction, wherein the forward strand-specific primers comprise universal sequence B;
   combining a second portion of the ligated nucleic acid samples with a biotin-labeled common primer A and: one or more reverse strand-specific primers in a second test reaction, wherein the reverse strand-specific primers comprise universal sequence B;
   subjecting each test reaction to amplification to generate a first set of amplicons;
   enriching the first set of amplicons by pooling the first set of amplicons together and then binding the pooled first set of amplicons to streptavidin-coated beads; and
   subjecting a portion of the first set of amplicons to a second round of amplification using common primer A and common primer B to generate a final set of amplicons.

2. The method of claim 1, further comprising at least one additional set of forward strand-specific primers in at least one additional test reaction.

3. The method of claim 1, further comprising at least one additional set of reverse strand-specific primers in at least one additional test reaction.

4. The method of claim 1, wherein the nucleic acid sample is derived from genomic DNA and wherein the method further comprises the step of, prior to ligation of the partially double-stranded blocking adapters, fragmenting nucleic acids from genomic DNA and subjecting the fragments to end-repair and dA-tailing.

5. The method of claim 4, wherein the nucleic acids are fragmented by a methodology selected from the group consisting of: physical shearing, chemical treatment and enzymatic treatment.

6. The method of claim 1, wherein the nucleic acid sample is derived from RNA and wherein the method further comprises, prior to ligation of partially double-stranded blocking adapters, subjecting the RNA to a reverse transcription reaction to generate double-stranded cDNA.

7. The method of claim 6, wherein the method further comprises the step of, prior to ligation of the partially double-stranded blocking adapters, subjecting the cDNA to end-repair and dA-tailing.

8. The method of claim 1, wherein the method further comprises the step of subjecting the final set of amplicons to next-generation sequencing.

9. The method of claim 8, further comprising the steps of analyzing the sequence data by a software algorithm and measuring allele counts at polymorphic sites.

10. The method of claim 1, wherein strand L of the partially double-stranded blocking adapters further comprises a barcode sequence at the 5' end.

11. The method of claim 1, wherein strand L of the partially double-stranded blocking adapters further comprises a unique molecular identifier.

12. The method of claim 1, wherein the one or more nucleic acid samples consist of nucleic acid selected from the group consisting of: circulating cfDNA and circulating ctDNA.

13. The method of claim 1, wherein each of the one or more nucleic acids samples is a mixture of maternal cfDNA and cffDNA from a pregnant woman.

14. The method of claim 1, wherein the nucleic acid sequences targeted by the at least one forward strand-specific primer and at least one reverse strand-specific primer comprise one or more mutations that are associated with disease.

15. A kit comprising:
   at least one partially double-stranded blocking adapter, wherein strand L of the at least one partially double-stranded blocking adapter comprises a barcode and a universal sequence A;
   at least one forward strand-specific primer;
   at least one reverse strand-specific primer;
   a biotin-labeled common primer A; and
   common primer A and common primer B;
   wherein the at least one forward strand-specific primer and at least one reverse strand-specific primer each comprise universal sequence B.

* * * * *